(12) United States Patent
Xi et al.

(10) Patent No.: US 9,320,448 B2
(45) Date of Patent: Apr. 26, 2016

(54) SYSTEMS AND METHODS FOR IMPROVED ATRIAL FIBRILLATION (AF) MONITORING

(75) Inventors: Cecilia Qin Xi, San Jose, CA (US); Cem Shaquer, Los Gatos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1660 days.

(21) Appl. No.: 12/106,043

(22) Filed: Apr. 18, 2008

(65) Prior Publication Data
US 2009/0264783 A1    Oct. 22, 2009

(51) Int. Cl.
*A61B 5/0456*   (2006.01)
*A61B 5/046*    (2006.01)

(52) U.S. Cl.
CPC .................................. *A61B 5/046* (2013.01)

(58) Field of Classification Search
USPC .................. 600/508, 509, 513, 518, 520, 521
See application file for complete search history.

(56) References Cited

U.S. PATENT DOCUMENTS

| | | | |
|---|---|---|---|
| 4,390,021 A | 6/1983 | Spurrell |
| 4,393,877 A | 7/1983 | Imran |
| 4,686,988 A | 8/1987 | Sholder |
| 4,708,142 A | 11/1987 | DeCote, Jr. |
| 4,712,555 A | 12/1987 | Thornander et al. |
| 4,729,376 A | 3/1988 | DeCote, Jr. |
| 4,788,980 A | 12/1988 | Mann et al. |
| 4,809,697 A | 3/1989 | Causey, III et al. |
| 4,872,459 A | 10/1989 | Pless |
| 4,938,228 A | 7/1990 | Righter |
| 4,940,052 A | 7/1990 | Mann et al. |
| 4,940,952 A | 7/1990 | Kegasa |
| 4,944,298 A | 7/1990 | Sholder |
| 4,944,299 A | 7/1990 | Silvian |
| 4,969,465 A | 11/1990 | Pless et al. |
| 4,969,467 A | 11/1990 | Callaghan et al. |
| 4,971,058 A | 11/1990 | Pless et al. |
| 5,065,759 A | 11/1991 | Begemann et al. |
| 5,074,302 A | 12/1991 | Poore et al. |
| 5,113,869 A | 5/1992 | Nappholz et al. |
| 5,133,350 A | 7/1992 | Duffin |
| 5,144,949 A | 9/1992 | Olson |

(Continued)

FOREIGN PATENT DOCUMENTS

| | | |
|---|---|---|
| WO | 00/64336 A1 | 11/2000 |
| WO | 00/71202 A1 | 11/2000 |

(Continued)

OTHER PUBLICATIONS

Non-Final Office Action mailed Feb. 23, 2009: Related U.S. Appl. No. 11/561,267.

(Continued)

*Primary Examiner* — Erica Lee
(74) *Attorney, Agent, or Firm* — Theresa A. Raymer

(57) ABSTRACT

Methods and systems described herein are especially useful wherein monitoring for atrial fibrillation (AF) is based on RR interval variability as measured from an electrocardiogram (ECG) signal. An activity threshold, which can be patient specific, is obtained. Patient activity is monitored. Based on the monitored patient activity and the activity threshold, there is a determination of when it is likely that AF monitoring based on RR interval variability is adversely affected by patient activity. When it has been determined that it is likely that AF monitoring based on RR interval variability is adversely affected by patient activity, whether and/or how AF monitoring is performed is modified.

21 Claims, 17 Drawing Sheets

(56) References Cited

U.S. PATENT DOCUMENTS

| | | | |
|---|---|---|---|
| 5,231,986 A * | 8/1993 | Bennett | 607/11 |
| 5,284,491 A | 2/1994 | Sutton et al. | |
| 5,292,340 A | 3/1994 | Crosby | |
| 5,327,900 A | 7/1994 | Mason | |
| 5,330,513 A * | 7/1994 | Nichols et al. | 607/32 |
| 5,350,410 A | 9/1994 | Kleks et al. | |
| 5,370,667 A | 12/1994 | Alt | |
| 5,403,355 A | 4/1995 | Alt | |
| 5,423,867 A | 6/1995 | Poore et al. | |
| 5,431,685 A | 7/1995 | Alt | |
| 5,458,622 A | 10/1995 | Alt | |
| 5,549,649 A | 8/1996 | Florio | |
| 5,720,769 A | 2/1998 | Van Ort et al. | |
| 5,738,104 A | 4/1998 | Lo | |
| 5,987,352 A | 11/1999 | Klein et al. | |
| 6,045,513 A | 4/2000 | Stone et al. | |
| 6,081,747 A | 6/2000 | Levine | |
| 6,102,874 A | 8/2000 | Stone et al. | |
| 6,120,467 A * | 9/2000 | Schallhorn | 600/595 |
| 6,275,734 B1 | 8/2001 | McClure et al. | |
| 6,280,409 B1 | 8/2001 | Stone et al. | |
| 6,285,907 B1 | 9/2001 | Kramer | |
| 6,361,503 B1 | 3/2002 | Starobin et al. | |
| 6,411,848 B2 | 6/2002 | Kramer | |
| 6,438,408 B1 | 8/2002 | Mulligan et al. | |
| 6,477,420 B1 | 11/2002 | Struble | |
| 6,501,988 B2 | 12/2002 | Kramer | |
| 6,529,771 B1 | 3/2003 | Kieval et al. | |
| 6,648,829 B2 | 11/2003 | Starobin et al. | |
| 6,648,830 B2 | 11/2003 | Starobin et al. | |
| 6,904,313 B1 | 6/2005 | Snell | |
| 6,922,584 B2 | 7/2005 | Wang et al. | |
| 7,031,766 B1 | 4/2006 | Paris | |
| 7,043,294 B1 | 5/2006 | Paris | |
| 7,142,918 B2 | 11/2006 | Stahmann | |
| 7,149,568 B2 | 12/2006 | Amano | |
| 7,187,965 B2 | 3/2007 | Bischoff et al. | |
| 7,192,401 B2 | 3/2007 | Saalasti | |
| 7,330,752 B2 | 2/2008 | Kettunen | |
| 7,676,262 B1 * | 3/2010 | Xi et al. | 600/519 |
| 2001/0016759 A1 | 8/2001 | Kramer | |
| 2002/0082648 A1 | 6/2002 | Kramer | |
| 2002/0082660 A1 | 6/2002 | Stahmann | |
| 2002/0115939 A1 | 8/2002 | Mulligan et al. | |
| 2002/0151806 A1 | 10/2002 | Starobin et al. | |
| 2002/0151811 A1 | 10/2002 | Starobin et al. | |
| 2003/0069610 A1 | 4/2003 | Kramer | |
| 2003/0074029 A1 | 4/2003 | Deno et al. | |
| 2003/0149370 A1 | 8/2003 | Starobin | |
| 2003/0187479 A1 | 10/2003 | Thong | |
| 2003/0208106 A1 | 11/2003 | Anderson et al. | |
| 2004/0010201 A1 * | 1/2004 | Korzinov et al. | 600/518 |
| 2005/0065443 A1 | 3/2005 | Ternes | |
| 2005/0187585 A1 | 8/2005 | Mussig | |
| 2006/0238333 A1 * | 10/2006 | Welch et al. | 340/539.12 |
| 2008/0081958 A1 * | 4/2008 | Denison et al. | 600/300 |
| 2008/0300641 A1 * | 12/2008 | Brunekreeft et al. | 607/6 |

FOREIGN PATENT DOCUMENTS

| | | |
|---|---|---|
| WO | 02/051496 A2 | 7/2002 |
| WO | 02/051496 A3 | 7/2002 |
| WO | 02/053026 A2 | 7/2002 |
| WO | 02/053026 A3 | 7/2002 |
| WO | 02/053228 A1 | 7/2002 |
| WO | 03/057032 A1 | 7/2003 |
| WO | 03/057033 A1 | 7/2003 |

OTHER PUBLICATIONS

Non-Final Office Action mailed Sep. 29, 2005: Related U.S. Appl. No. 10/828,897.
Non-Final Office Action mailed Oct. 13, 2005: Related U.S. Appl. No. 10/828,883.
Notice of Allowance mailed Jan. 20, 2006: Related U.S. Appl. No. 10/828,897.
Notice of Allowance mailed Jan. 10, 2006: Related U.S. Appl. No. 10/828,883.
Non-Final Office Action mailed Jun. 26, 2009: Related U.S. Appl. No. 11/351,401.
Non-Final Office Action mailed Jul. 10, 2009: Related U.S. Appl. No. 11/351,859.
Notice of Allowance Action mailed Jan. 15, 2010: Related U.S. Appl. No. 11/405,129.
Amendment filed Dec. 7, 2009: Related U.S. Appl. No. 11/405,129.
Final Office Action mailed Oct. 7, 2009: Related U.S. Appl. No. 11/405,129.
Amendment filed Jul. 1, 2009: Related U.S. Appl. No. 11/405,129.
Non-Final Office Action mailed Apr. 1, 2009: Related U.S. Appl. No. 11/405,129

* cited by examiner

702

```
┌─────────────────────────────────────────────────────────┐
│         determine activity threshold time period         │─── 902
└─────────────────────────────────────────────────────────┘
                            │
                            ▼
┌─────────────────────────────────────────────────────────┐
│ partition activity threshold time period into a plurality of first │─── 904
│                    sub-time period                       │
└─────────────────────────────────────────────────────────┘
                            │
                            ▼
┌─────────────────────────────────────────────────────────┐
│   partition each first sub-time periods into a plurality of │─── 906
│                  second sub-time periods                 │
└─────────────────────────────────────────────────────────┘
                            │
                            ▼
┌─────────────────────────────────────────────────────────┐
│  for each second sub-time period, periodically measure HR │
│                  and activity level and:                 │
│  1) calculate $HR_{reserve}$, and 2) calculate CORR;     │─── 908
│         determine the CORR. appearing most frequent; and │
│  set a second sub-time period activity threshold at X%   │
│              above the most frequent CORR.               │
└─────────────────────────────────────────────────────────┘
                            │
                            ▼
┌─────────────────────────────────────────────────────────┐
│   for each first sub-time period, save the median of the │─── 910
│   second sub-time period activity thresholds as the first sub- │
│             time period activity threshold              │
└─────────────────────────────────────────────────────────┘
                            │
                            ▼
┌─────────────────────────────────────────────────────────┐
│ at the end of the activity threshold time period, set the │─── 912
│ patient specific activity threshold (PS ACT THR) equal to │
│ the average of the first sub-time period activity thresholds │
└─────────────────────────────────────────────────────────┘
```

*FIG. 9*

SYSTEMS AND METHODS FOR IMPROVED ATRIAL FIBRILLATION (AF) MONITORING

RELATED APPLICATION

The present application is related to commonly assigned U.S. patent application Ser. No. 11/405,129, filed Apr. 13, 2006, entitled "Methods and Devices for Determining Exercise Compliance Diagnostics," which is incorporated herein by reference, now U.S. Pat. No. 7,676,262.

FIELD OF THE INVENTION

Embodiments of present invention relate to monitoring for atrial fibrillation (AF), and implantable and non-implantable systems that perform such monitoring.

BACKGROUND

Atrial Fibrillation (AF) is a very common supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner. To overcome this, many cardiac devices now monitor for AF. For example, ambulatory cardiac devices, such as Holter monitors, typically monitor for AF by obtaining an electrocardiogram (ECG) signal and measuring RR interval variability based on the ECG signal. For example, the device can compare measures of RR interval variability (or in increase compared to a baseline variability) to a variability threshold, to automatically detect AF when the variability threshold is exceeded. Implantable cardiac devices that obtain an ECG signal from subcutaneous (subQ) extra-cardiac electrodes typically monitor for AF in the same manner.

The reason such devices rely on measures of RR interval variability for AF monitoring, as opposed relying on measures of P-waves, is that such devices can not accurately detect P-waves due to small P-wave amplitude and relative high noise level, which leads to poor signal-to-noise ratio. In contrast, such devices can detect R-waves with good accuracy.

A problem AF monitoring based on RR interval variability is that other factors, besides AF, can result in increases in measurements of RR interval variability. This leads to high false detections of AF, which can lead to inappropriate diagnosis and/or inappropriate treatment.

SUMMARY

Methods and systems described herein are especially useful where monitoring for atrial fibrillation (AF) is based on RR interval variability as measured from an electrocardiogram (ECG) signal. In accordance with an embodiment, an activity threshold, which is preferably a patient specific activity threshold, is obtained. Patient activity is monitored. Based on the monitored patient activity and the activity threshold, there is a determination of when it is likely that AF monitoring based on RR interval variability is adversely affected by patient activity. When it has been determined that it is likely that AF monitoring based on RR interval variability is adversely affected by patient activity, whether and/or how AF monitoring is performed can be modified.

In accordance with an embodiment, the monitored patient activity is compared to the patient specific activity threshold. When the monitored patient activity exceeds the patient specific activity threshold, it is determined that it is likely that AF monitoring based on RR interval variability is adversely affected.

In accordance with an alternative embodiment, activity correlation values are determined based on the monitored patient activity and corresponding heart rate data. The activity correlation values are compared to the patient specific activity threshold. When the activity correlation values exceed the patient specific activity threshold, it is determined that it is likely that AF monitoring based on RR interval variability is adversely affected.

When it has not been determined that it is likely that that AF monitoring based on RR interval variability is adversely affected, monitoring for AF can be based on RR interval variability as measured from an ECG signal.

When it has been determined that it is likely that that AF monitoring based on RR interval variability is adversely affected, whether and/or how AF monitoring is performed can be modified. In one embodiment, AF monitoring can be inhibited. In another embodiment, detected episodes of AF can be ignored. In a further embodiment, information about detected episodes of AF can be stored along with an indication that the detected episodes of AF were detected during elevated patient activity.

This description is not intended to be a complete description of, or limit the scope of, the invention. Other features, aspects, and objects of the invention can be obtained from a review of the specification, the figures, and the claims.

BRIEF DESCRIPTION OF DRAWINGS

FIG. 9 is a high level flow diagram that describes a method for determining a patient specific activity threshold that can be used in the method of FIG. 7.

DETAILED DESCRIPTION

The following description is of the best modes presently contemplated for practicing various embodiments of the present invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Before going into specific details regarding the various embodiments of the present invention, it is first useful to describe an exemplary implantable system, and an exemplary ECG signal that may be sensed by an implantable system. Although an implantable system is illustrated, embodiments of the present invention can also be implemented using an external cardiac monitor (e.g., a Holter device) or an external automatic defibrillator that obtains an ECG signal using surface electrodes. Accordingly, embodiments of the present invention are also directed to non-implanted devices and systems that implement features of one or more embodiment of the present invention.

Overview of Extracardiac/Extravascular Defibrillation System

Figure 1:
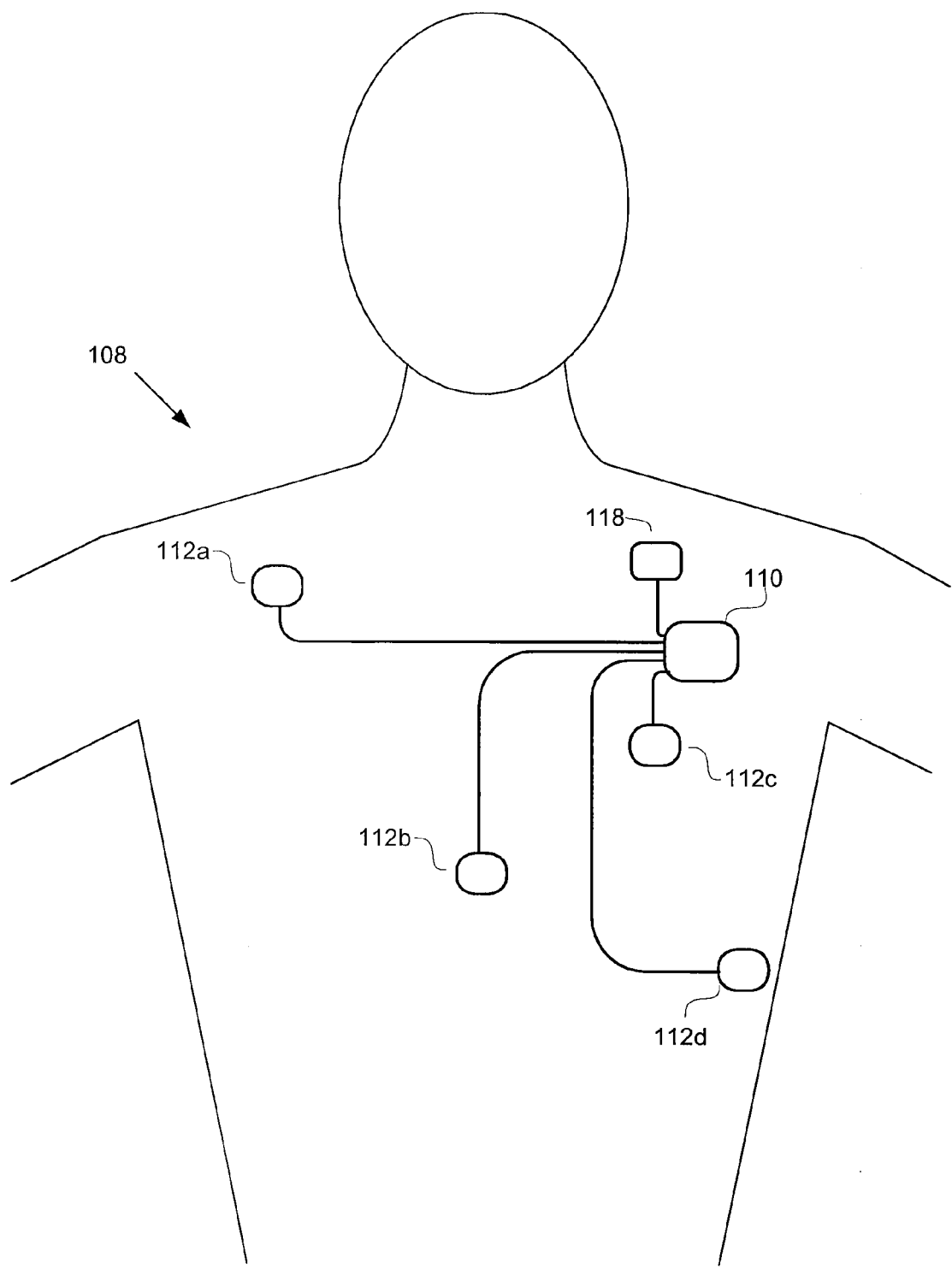
FIG. 1 illustrates components of an exemplary extracardiac/extravascular cardiac stimulation system in which embodiments of the present invention can be useful.

Referring first to FIG. 1, an exemplary implantable extracardiac system 108 includes a subcutaneous (subQ) device 110 and multiple subQ extracardiac electrodes 112 (also referred to as remote sensing electrodes) for detecting electrical cardiac signals within the chest of the patient. The subQ extracardiac electrodes 112 are preferably extravascular and can be, e.g., paddle electrodes or coil electrodes mounted subcutaneously outside of the rib cage, but are not limited thereto. Exemplary locations of the subQ extracardiac electrodes 112 include near the bottom of the sternum (slightly to the left), below the left pectoral area, and below the clavicle and on the back left side (just below the shoulder blade). Of course, additional and/or alternative locations for subQ electrodes 112 are within the scope of the present invention. For example, one or more SubQ electrode can be located on the housing of the device.

The subQ device 110 can be an implantable cardioverter defibrillator (ICD) and/or a pacemaker. It is also possible that the device 110 can be a monitor that does not have any stimulation capabilities. Exemplary details of the subQ device 110 are discussed below with reference to FIG. 3.

An activity sensor 118 is also shown in FIG. 1. While shown as being external to the housing of the device 110, it is also within the scope of the present invention that the activity sensor 118 can be located within the housing (also known as "can") of the device 110. Exemplary activity sensors are disclosed in the following patents, which are each incorporated herein by reference: U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position."

In certain embodiments, the activity sensor 118 is a one-dimensional activity sensor, such as a sensor that incorporates a piezoelectric crystal which generates a measurable electrical potential when a mechanical stress resulting from physical activity is applied to the sensor. U.S. Pat. No. 4,140,132 to Dahl and U.S. Pat. No. 4,428,378 to Anderson et al., which are incorporated herein by reference, describe implantable devices that measure patient activity using a piezoelectric sensor incorporating a piezoelectric crystal. Besides piezoelectric crystals, other piezoelectric activity sensors detect activity using a cantilever beam having a film of a piezoelectric polymer adhered to a surface of the beam. Examples of such cantilever type activity sensor are described in U.S. Pat. No. 5,833,713 to Moberg and U.S. Pat. No. 5,383,473 to Moberg, which are incorporated herein by reference.

Piezoelectric activity sensors are passive devices, meaning they do not require an external excitation current or voltage to operate. Rather, they convert mechanical motion into a detectable electrical signal, such as a back electro magnetic field (BEMF) current or voltage. Accordingly, such types of activity sensors are very useful with battery powered implantable devices where minimizing current drain and power consumption is critical.

Although an implantable subQ device 110 is illustrated and described, embodiments of the present invention could also be implemented in an external (i.e., non-implantable) ambulatory device such as a Holter monitor or an external automatic defibrillator.

Implantable Subcutaneous Device

Additional exemplary details of a subQ device 110 shall now be described with reference to FIG. 2, which is a simplified block diagram of the internal components of the subQ device 110. While particular details are shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. For example, where the device 110 only provides monitoring capabilities, components used for cardioversion, defibrillation and pacing stimulation can be eliminated.

Figure 2:
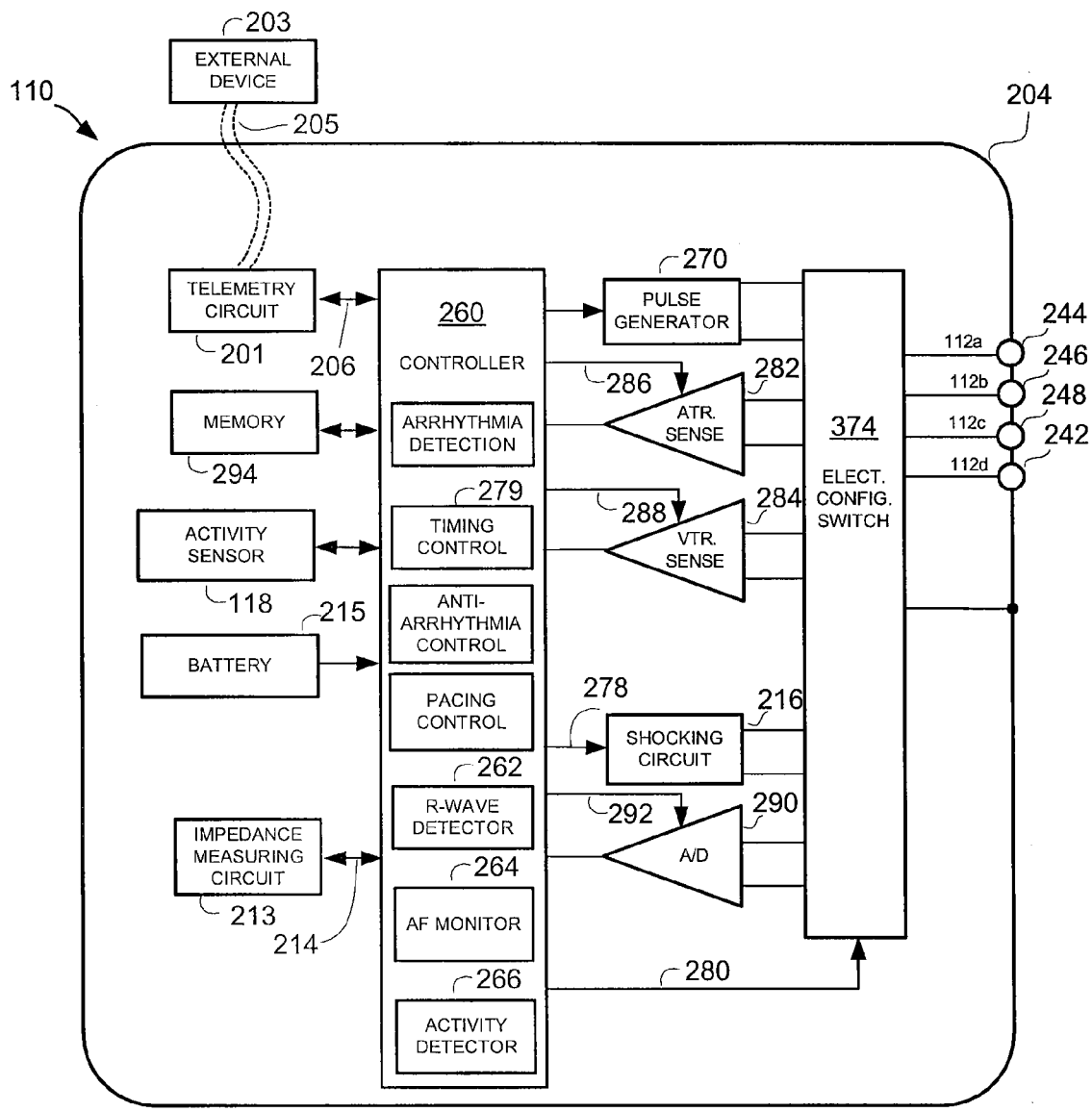
FIG. 2 is a high level diagram of a subcutaneous device, according to an embodiment of the present invention.

A housing 204 for the device 110, shown schematically in FIG. 2, (often referred to as the "can", "case" or "case electrode") may be programmably selected to act as the return electrode for all "unipolar" modes. The housing 204 may further be used as a return electrode alone or in combination with one or more electrodes 112 for shocking purposes. The housing 204 can further includes a connector (not shown) having a plurality of terminals, 242, 244, 246, 248 etc. (shown schematically and, for convenience, the reference numbers of the extracardiac subQ electrodes 112 to which they are connected are shown next to the terminals).

At the core of the device 110 is a programmable controller 260 which can control cardiac monitoring and various modes of cardiac stimulation therapy, including anti-arrhythmia therapy. As is well known in the art, the controller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the controller 260 includes the ability to analyze signals (data) as controlled by a program code stored in a designated block of memory. The details of the design of the controller 260 are not critical to the present invention. Rather, any suitable controller 260 can be used to carry out the functions described herein. The use of microprocessor-based control circuits for performing timing and data analysis functions are well known in the art.

In specific embodiment of the present invention, the controller 260 performs some or all of the steps associated with monitoring for AF, detecting R-waves, defining threshold levels, and the like. Accordingly, the controller is shown as including an AF monitor block 264 and an R-wave detection block 262. The controller can also include an activity monitor 266, which can, e.g., compare patient activity (or values based thereon) as detected by the activity sensor 118 to an activity threshold. While shown as being implemented as part of the controller, the AF monitor 264 and/or the activity monitor 266 can be implemented partially or entirely separate from the controller 260, e.g., using hardware, firmware, or software, or combinations thereof.

Exemplary types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the device and their inter-relationship, see U.S. Pat. No. 4,788,980 (Mann et. al.). The '052, '555, '298 and '980 patents are incorporated herein by reference.

As shown in FIG. 2, a pulse generator block 270 generates stimulation pulses for delivery by the subQ extracardiac electrodes 112. It is understood that in order to provide stimulation therapy in more than one chamber of the heart, the pulse generator block 270 may include dedicated, independent pulse generators, multiplexed pulse generators, or shared pulse generators. The pulse generator block 270 is controlled by the controller 260 via appropriate control signals to trigger or inhibit the stimulation pulses.

The controller 260 further includes timing control circuitry 279 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art.

A switch bank 274 includes a plurality of switches for connecting the desired subQ extracardiac electrodes 112 to the appropriate I/O circuits, thereby providing complete electrode programmability. Accordingly, the switch bank 274, in response to a control signal 280 from the controller 260, determines the polarity of the stimulation pulses (e.g., unipolar, bipolar, combipolar, etc.) by selectively closing the appropriate combination of switches (not specifically shown) as is known in the art.

Sensing circuits 282 and 284 may also be selectively coupled to the various subQ extracardiac electrodes 112 through the switch bank 274 for detecting the presence of cardiac activity from the heart. Accordingly, the sensing circuits, 282 and 284, may include dedicated sense amplifiers, multiplexed amplifiers, or shared amplifiers. The switch bank 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, filters (e.g., for low pass, high pass and/or band pass filtering), and a threshold comparison/detection circuit, as known in the art, to selectively sense the cardiac signal of interest. The automatic gain control enables the device 110 to deal effectively with the difficult problem of sensing the low amplitude signal characteristics of atrial or ventricular fibrillation. Thresholding, match filtering, sliding window correlation, and other types of signal analysis can also be performed within the controller 260.

The outputs of the sensing circuits, 282 and 284, are connected to the controller 260 which, in turn, are able to trigger or inhibit the pulse generator block 270 in a demand fashion in response to the absence or presence of cardiac activity. The sensing circuits, 282 and 284, in turn, receive control signals over signal lines, 286 and 288, from the controller 260 for purposes of measuring cardiac activity at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 utilizes the sensing circuits, 282 and 284, to sense cardiac signals to determine whether a rhythm is physiologic or pathologic. The timing intervals between sensed events (e.g., R-waves) are then classified by the controller 260, e.g., by comparing them to predefined or self calibrating (i.e., updating) rate zone limits (e.g., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 290. The data acquisition system 290 is configured to acquire electrocardiogram (ECG) signals, convert the raw analog data into a digital signal, and store the digital signals for later processing and/or telemetric transmission to an external device 203. The data acquisition system 290 is coupled to subQ extracardiac electrodes 112 through the switch bank 274 to sample cardiac signals across any pair of desired electrodes.

Advantageously, the data acquisition system 290 can be coupled to the controller 260, or other detection circuitry, for detecting an evoked response from the heart in response to an applied stimulus, thereby aiding in the detection of "capture". Capture occurs when an electrical stimulus applied to the heart is of sufficient energy to depolarize the cardiac tissue, thereby causing the heart muscle to contract. The controller 260 detects a depolarization signal during a window following a stimulation pulse, the presence of which indicates that capture has occurred. The controller 260 enables capture detection by triggering the pulse generator 270 to generate a stimulation pulse, starting a capture detection window using the timing control circuitry 279 within the controller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The controller 260 is further coupled to a memory 294 by a suitable data/address bus, wherein the programmable operating parameters used by the controller 260 are stored and modified, as required, in order to customize the operation of the device 110 to suit the needs of a particular patient. Such operating parameters define, for example, pacing pulse amplitude, pulse duration, electrode polarity, rate, sensitivity, automatic features, arrhythmia detection criteria, initial R-wave detection parameters, and the amplitude, waveshape and vector of each shocking pulse to be delivered to the patient's heart within each respective tier of therapy. The memory 294, or a further memory, can also be used to store information about detected episodes of AF and patient activity that is obtained by the device 110.

Advantageously, the operating parameters of the implantable device 110 may be non-invasively programmed into the memory 294 through a telemetry circuit 201 in telemetric communication with an external device 203, such as a programmer, transtelephonic transceiver, or a diagnostic system analyzer. The telemetry circuit 201 is activated by the controller 260 by a control signal 206. The telemetry circuit 201 advantageously allows intracardiac electrograms and status information relating to the operation of the device 110 (as contained in the controller 260 or memory 294) to be sent to the external device 203 through an established communication link 205.

Examples of telemetry circuits are described in the following U.S. patents, each of which is incorporated herein by reference: U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (note: this patent relates to transfer of EGM data) (McClure et al.). Another example of a telemetric circuit for use in a chronically implantable device is the TR1000 transceiver manufactured by RF Monolithics, Dallas, Tex. The TR 1000 is a single-chip, low-power, 916.5 MHz transceiver. An operating frequency of about 916.5 MHz is typically desirable because of the modest requirements on antenna size it imposes. Such telemetry circuits can use, e.g., magnetic induction, radio telemetry or acoustic telemetry.

In accordance with an embodiment, the device 110 further includes an activity sensor 118, which as mentioned above, can be located within the device housing 204 as shown in FIG. 2, or can be located external to the housing as shown in FIG. 1.

A battery 215 provides operating power to all of the circuits shown in FIG. 2. If the device 110 employs shocking therapy, the battery 215 should be capable of operating at low current drains for long periods of time, and then be capable of providing high-current pulses (for capacitor charging) when the patient requires a shock pulse. The battery 215 should also have a predictable discharge characteristic so that elective replacement time can be detected. Accordingly, the device 110 preferably employs lithium/silver vanadium oxide batteries, as is true for most (if not all) current devices, but is not limited thereto.

The device 110 can also include a magnet detection circuitry (not shown), coupled to the controller 260. It is the purpose of the magnet detection circuitry to detect when a magnet is placed over the device 110. The magnet may be used by a clinician to perform various test functions of the device 110 and/or to signal the controller 260 that the external programmer 203 is in place to receive or transmit data to the controller 260 through the telemetry circuits 201.

As further shown in FIG. 2, the device 110 is shown as having an impedance measuring circuit 213 which is enabled by the controller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 213 is advantageously coupled to the switch bank 274 so that any desired electrode may be used. In addition, to facilitate the measurement of peripheral tissue edema, extra electrodes can be added to the device housing, thereby limiting the test electric field to the peripheral tissue.

In the case where the device 110 is intended to operate as an implantable cardioverter defibrillator (ICD) device, it must detect the occurrence of an arrhythmia, and automatically apply an appropriate electrical shock therapy to the heart aimed at terminating the detected arrhythmia. To this end, the controller 260 further controls a shocking circuit 216 by way of a control signal 278. The shocking circuit 216 generates shocking pulses of low (up to 0.5 Joules), moderate (0.5-10 Joules), or high energy (11 to 40 Joules), as controlled by the controller 260. Such shocking pulses are applied to the patient's heart through at least two electrodes. As noted above, the housing 204 may act as an active electrode in combination with one of the subQ extracardiac electrodes 112.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognized), and pertaining exclusively to the treatment of fibrillation. Accordingly, the controller 260 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

Additional and alternative details of implantable cardiac devices can be found in U.S. Pat. No. 5,405,363 (Kroll et al.) and U.S. Pat. No. 5,040,534 (Mann et al.), both of which are incorporated herein by reference.

Exemplary ECG Waveform

Figure 3:
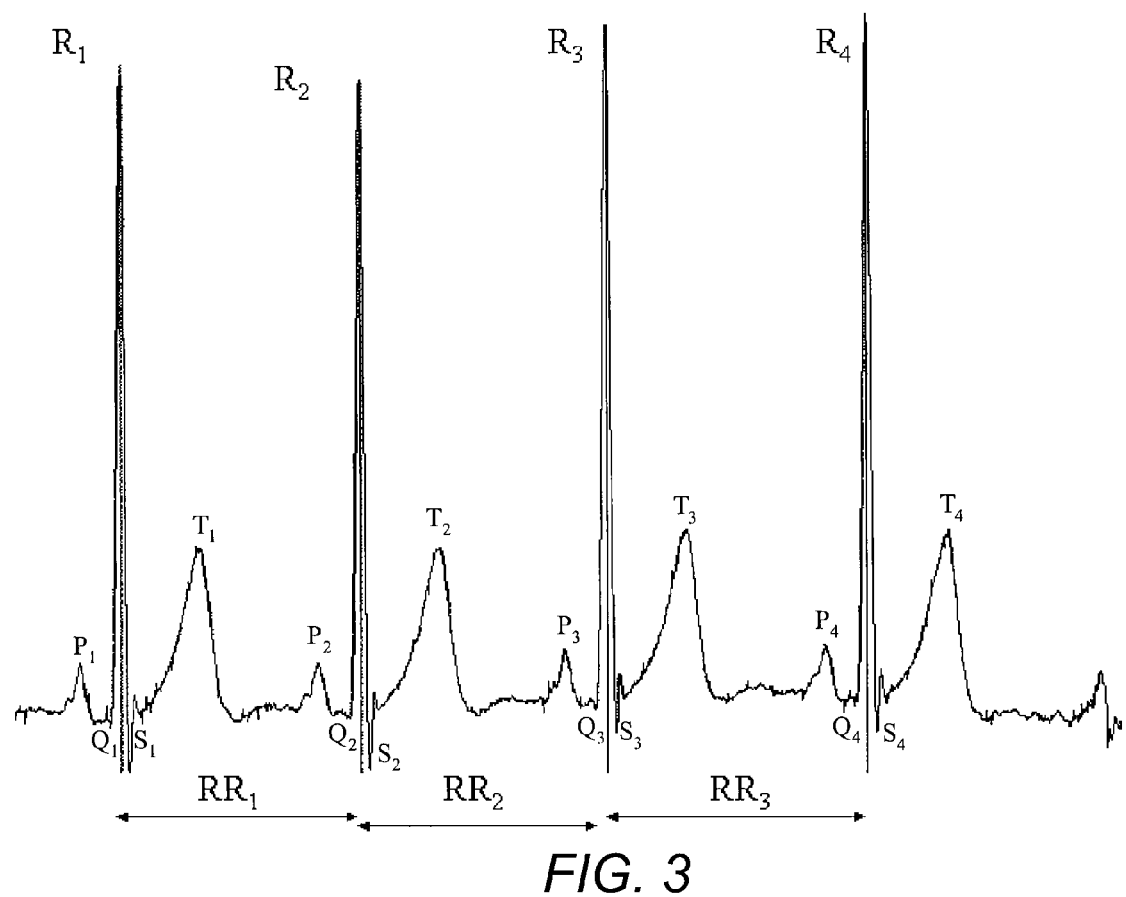
FIG. 3 illustrates a portion of an exemplary ECG waveform, with three consecutive RR intervals labeled $RR_1$, $RR_2$ and $RR_3$.

FIG. 3 illustrates an exemplary electrocardiogram (ECG) waveform, which is shown as including a P wave, a QRS complex (including Q, R and S waves) and a T wave. The P wave is caused by depolarization of the atria. This is followed by atrial contraction, which is indicated by a slight rise in the atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. The QRS complex includes a Q-wave, an R-wave and an S-wave, as shown in FIG. 3. Ventricular repolarization occurs thereafter, as indicated by the T wave and this is associated with the onset of ventricular relaxation in which forward flow stops, the pressure in the ventricle falls below that in the atria at which time the mitral and tricuspid valves open to begin to passively fill the ventricle during diastole.

Various measurements can be obtained based on the ECG waveform, including measurements of RR intervals, where an RR interval is the duration between a pair of consecutive R waves. In FIG. 3, three consecutive RR intervals are labeled RR1, RR2 and RR3. While P-waves are recognizable in FIG. 3, P-waves are typically difficult to accurately detect from an ECG signal. That is why AF monitoring based on measures from an ECG signal is typically performed based on measures of RR interval variability, otherwise known as heart rave variability (HRV). This can be accomplished, e.g., by comparing the measures of RR interval variability (or in increase compared to a baseline variability) to a variability threshold, to automatically detect AF when the variability threshold is exceeded. External (ambulatory) cardiac devices, such as Holter monitors, typically monitor for AF using the same technique. A problem with such AF monitoring is that other factors, besides AF, can result in increases in measurements of RR interval variability. For a specific example, patient activity can cause increases in RR interval variability, even though the patient is not experiencing AF. This leads to high false detections of AF, which can lead to inappropriate diagnosis and/or inappropriate treatment. Embodiments of the present invention, as will be appreciated from the discussion below, can be used to reduce the probability of such false AF detections. More generally, embodiments of the present invention can be used to improve AF monitoring.

Exemplary R-Wave Detection

To measure RR intervals, R-waves need to be detected. There are many known techniques for detecting R-waves. However, for completeness, some exemplary techniques for detecting R-waves are provided below. However, it is noted that embodiments of the present invention should not be limited to use with the following R-wave detection techniques.

Figure 4A:
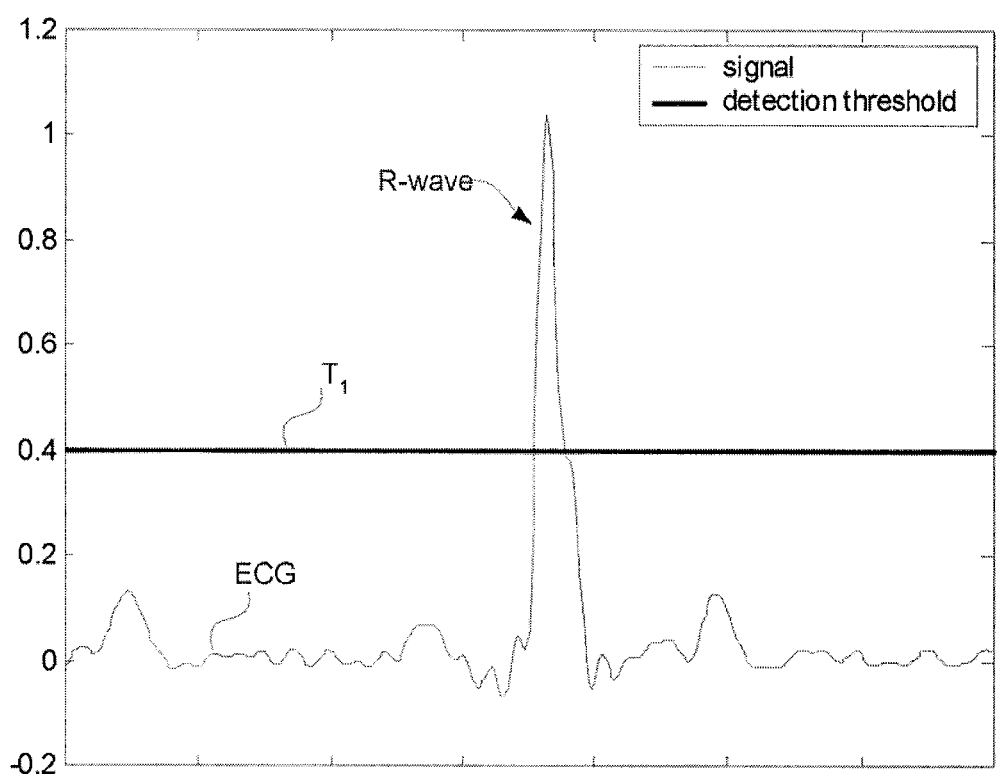
FIGS. 4A-4E illustrate graphs that are useful for describing various exemplary R-wave detection schemes.

The graph of FIG. 4A is used to describe a simple conventional R-wave detection scheme in which an R-wave detection occurs whenever the ECG waveform exceeds a constant detection threshold $T_1$ (e.g., 0.4 mV). However, the mean amplitudes of ECG signals sensed (i.e., detected) using extracardiac subQ electrodes (e.g., 112) or surface electrodes can tend to change over time, e.g., due to movement of the electrodes, intermittent contact problems, tissue growth over the electrodes, changes in breathing, etc. Such sensing issues are particularly problematic when the sensing electrodes are far and spatially removed from the heart, such as in the case of extracardiac subQ electrodes. Accordingly, it may be beneficial for the R-wave detection scheme to adapt to changes in ECG signal trends.

Figure 4B:
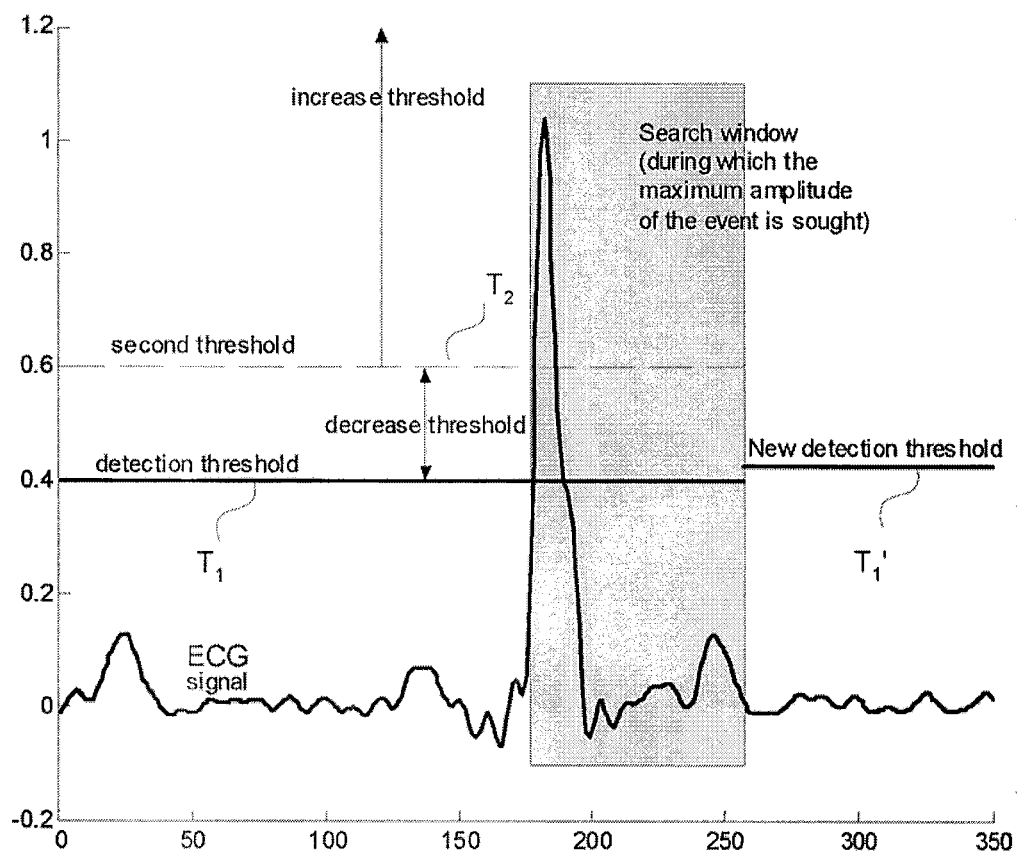

The graph of FIG. 4B is used to describe a first adaptive scheme for detecting R-waves. These R-wave detection features, as well as the features of the further R-wave detection schemes described with reference to FIGS. 4C-4E, can be performed, e.g., by the R-wave detector 362 shown in FIG. 3. In this embodiment, there is a first threshold $T_1$, also referred to as the adjustable R-wave detection threshold and a higher second threshold $T_2$, which is used to quantify the amplitude of the cardiac event represented by the ECG waveform. The second threshold $T_2$ can be set as a predetermined value (e.g., 0.2V) or a predetermined percentage (e.g., 50%) greater than the present detection threshold $T_1$. In the graph of FIG. 4B, the detection threshold $T_1$ is initially shown as being equal to 0.4 mV, and the second threshold $T_2$ is shown as being equal to 0.6 mV (e.g., $T_2=T_1+0.2$ mV; or $T_2=T_1+(0.5*T_1)$). In accordance with this embodiment, during a window (of fixed or non-fixed width) following an R-wave detection, there is a determination of whether the second threshold $T_2$ is exceeded. If the second threshold $T_2$ is exceeded, as shown in FIG. 4B, then the detection threshold $T_1$ is increased (e.g., by a predefined value or percentage) to define an updated detection threshold $T_1'$. If the second threshold $T_2$ is not exceeded, then the detection threshold $T_1$ is decreased, e.g., by another (or the same) predefined value or percentage. The amount of the increase and the amount of the decrease used determines how fast the detection threshold $T_1$ adapts to signal trends.

Figure 4C:
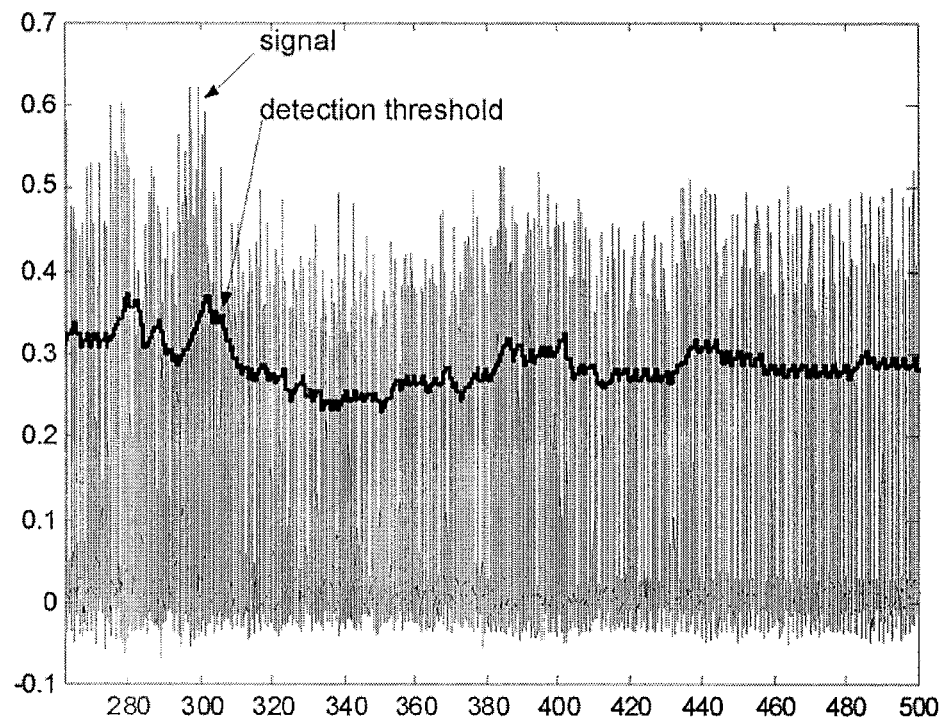

FIG. 4C shows how this technique performs in a specific case where: the detection threshold $T_1$ is increased by 2.1% when the second threshold $T_2$ is exceeded; the detection threshold is decreased by 4.2% when the second threshold $T_2$ is not exceeded; and where the second threshold $T_2$ is set to be 43% higher than the detection threshold $T_1$, giving a safety margin of approximately 30%.

Figure 4D:
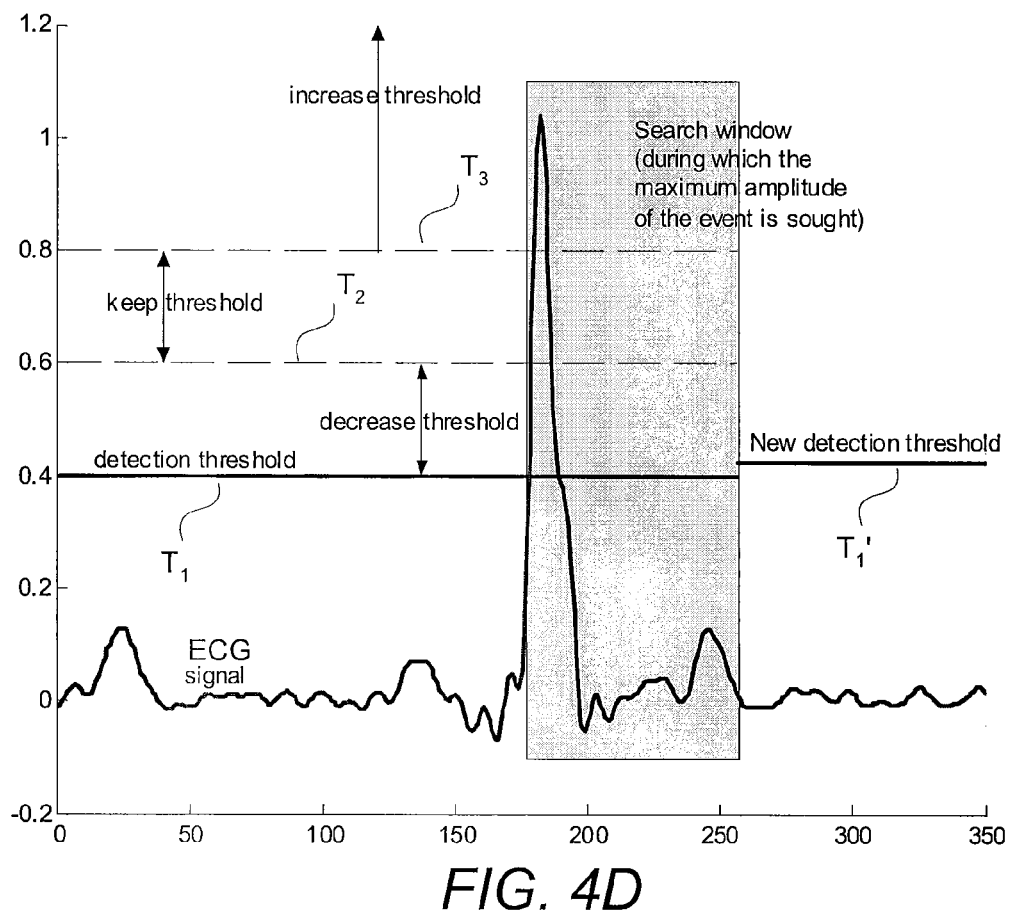

The graph of FIG. 4D is used to describe another embodiment for detecting R-waves. In this embodiment, there is a first threshold $T_1$, also referred to as the adjustable detection threshold, a higher second threshold $T_2$, and an even higher third threshold $T_3$, with the second and third thresholds being used to quantify the amplitude of the cardiac event represented by the ECG waveform. In the graph of FIG. 4D, the detection threshold $T_1$ is initially shown as being equal to 0.4 mV, the second threshold $T_2$ is shown as being equal to 0.6 mV (e.g., $T_2=T_1+0.2$ mV; or $T_2=T_1+(0.5*T_1)$) and the third threshold $T_3$ is shown as being equal to 0.8 mV (e.g., $T_3=T_1+0.4$ mV; or $T_2=2*T_1$). In accordance with this embodiment, during a window following an R-wave detection, there is a determination of whether the second threshold $T_2$ and the third threshold $T_3$ are exceeded. If the second threshold $T_2$ and the third threshold $T_3$ are both exceeded, as shown in FIG. 4D, then the detection threshold $T_1$ is increased, e.g., by a predefined value or percentage, to define an updated detection threshold $T_1'$. If the second threshold $T_2$ is not exceeded, then the detection threshold $T_1$ is decreased, e.g., by another (or the same) predefined value or percentage. If the second threshold $T_2$ is exceeded, but the third threshold $T_3$ is not exceeded, then the first threshold is kept the same. The amount of the increase and the amount of the decrease used determines how fast the detection threshold $T_1$ adapts to signal trends.

Figure 4E:
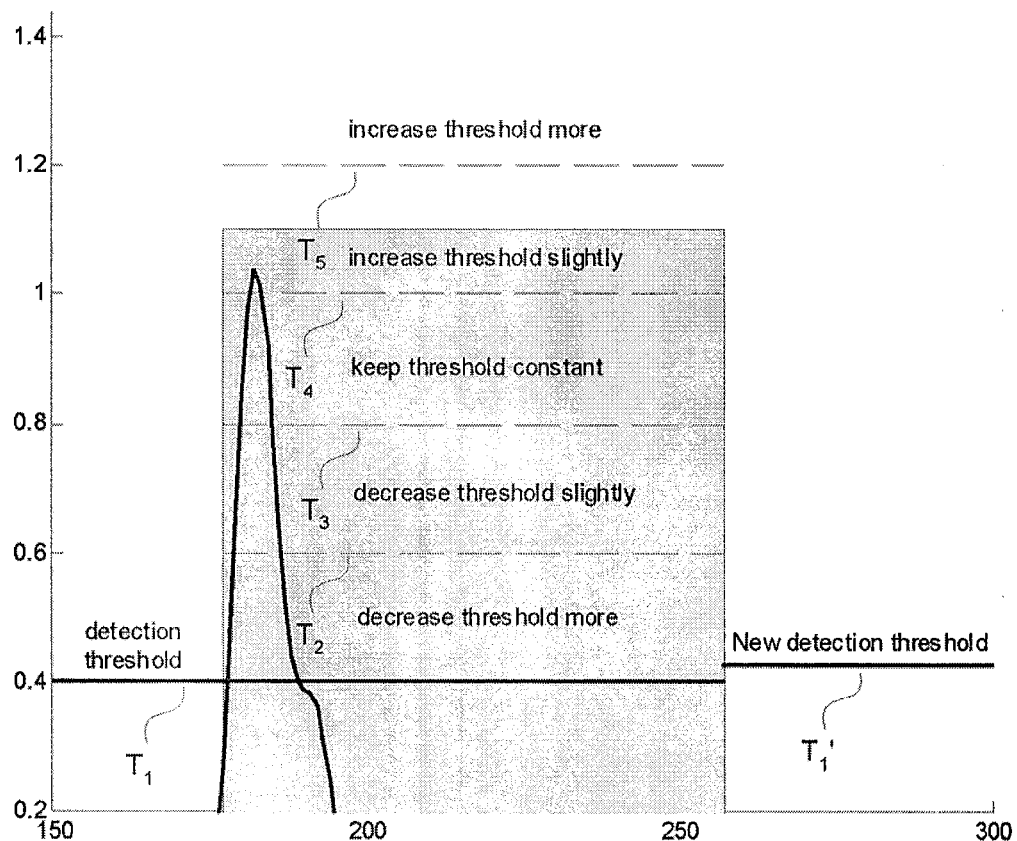

A further expansion of the embodiments discussed above is to use additional thresholds to divide the region above the detection threshold $T_1$ into even more parts, and to differently change the detection threshold $T_1$ depending on which amplitude(s) are exceeded. For example, as shown in FIG. 4E, there can be a detection threshold $T_1$ and four additional thresholds $T_2$, $T_3$, $T_4$ and $T_5$. In accordance with such an embodiment, if the second threshold $T_2$ is not exceeded, then the detection threshold $T_1$ would be decreased by an amount (e.g., a value or percentage). If the second threshold $T_2$ is exceeded, but the third threshold $T_3$ is not exceeded, then the detection threshold $T_1$ would be decreased by a lesser amount (e.g., a lesser value or percentage). If the third threshold $T_3$ is exceeded, but the fourth threshold $T_4$ is not, then the detection threshold $T_1$ would be kept constant. If the fourth threshold $T_4$ is exceeded, but the fifth threshold $T_5$ is not exceeded, then the detection threshold $T_1$ would be increased by an amount (e.g., a value or percentage). If the fifth threshold $T_5$ is exceeded, then the detection threshold $T_1$ would be increased by a greater amount (e.g., a greater value or percentage).

In still another embodiment, the region above the detection threshold is divided into an infinite number or regions. More specifically, the change in the detection threshold is set as a linear function of the maximum amplitude during a window of time (of fixed or non-fixed width) following an R-wave detection, using the formula: $\Delta$ detection threshold=k*(max amplitude−second threshold), where k is a scaling factor that can be set to any positive number, and the second threshold defines the point at which the detection threshold is either increased, kept constant, or decreased (i.e., if the maximum amplitude is greater then the second threshold, then $\Delta$ detection threshold will be a positive amount; if the maximum amplitude is equal to the second threshold, then $\Delta$ detection threshold will be zero; and if the maximum amplitude is less than the second threshold, then $\Delta$ detection threshold will be a negative amount). The second threshold is preferably a function of the detection threshold, e.g., a percentage of the detection threshold, or the detection threshold plus a constant. For example, if the second threshold=1.5*detection threshold, then the safety margin will be approximately 1−(1/1.5) =0.33=33%.

By using the above described schemes for adjusting the R-wave detection threshold, the region where the detection threshold becomes relatively stable is driven to the mean amplitude of the detections. Thus, the second threshold or whatever specifies the signal amplitude at which the detection threshold is unchanged is tightly linked to the safety margin of the system.

Atrial Fibrillation (AF) Monitoring

Figure 5:
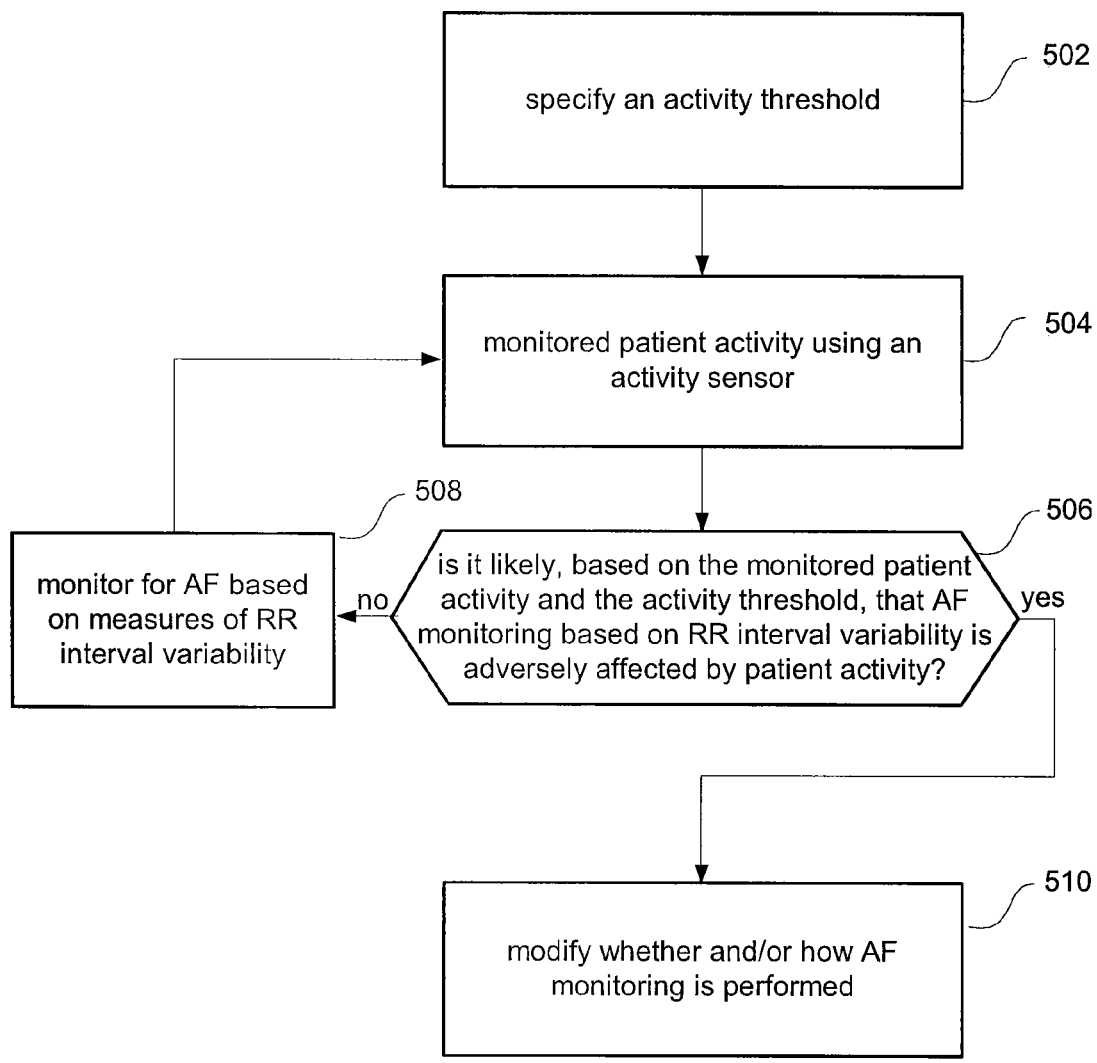
FIG. 5 is a high level flow diagram that describes a method for improved AF monitoring, according to an embodiment of the present invention.

The high level flow diagram of FIG. 5 will now be used to describe embodiments of the present invention where patient activity is taken into account when monitoring for AF based on an electrocardiogram (ECG) signal.

Referring to FIG. 5, at step 502, an activity threshold is specified, or otherwise obtained. At step 504, patient activity is monitored, using an activity sensor (e.g., 118), many examples of which were discussed above. At step 506, there is a determination, based on the monitored patient activity and the activity threshold, of whether it is likely the AF monitoring based on RR interval variability is adversely affected by patient activity. For example, in one embodiment, at step 506 the monitored patient activity can be compared to the activity threshold to determine whether the patient activity exceeds the activity threshold. If the activity threshold is not exceeded, then it can be determined that it is not likely the AF monitoring based on RR interval variability is adversely affected by patient activity, and thus AF monitoring can be performed based on RR interval variability at step 508. If the activity threshold is exceeded, then it can be determined that it is likely the AF monitoring based on RR interval variability is adversely affected by patient activity.

In specific embodiments, the patient activity threshold would need to exceed the activity threshold for at least a specified duration (referred to as an entry duration) for there to be a determination that AF monitoring based on RR interval variability is adversely affected by patient activity. This would make the algorithm less sensitive to transient patient activity, e.g., due to a patient lifting a limb or sitting up, and thereby increase the likelihood that the device can distinguish transient activity from persistent activity. Further, in specific embodiments, after it has been determined that it is likely that AF monitoring based on RR interval variability is adversely affected, it can thereafter be determined that it is no longer likely that AF monitoring based on RR interval variability is adversely affected, when the monitored patient activity does not exceed the activity threshold for a further specified duration (referred to as the exit duration). Preferably the exit duration is longer than the entry duration. For example, the entry duration can be 20 seconds, and the exit duration can be 60 seconds. Such durations can be programmed into the device. The exemplary duration values are not meant to be limiting.

At step 508 monitoring for AF can be accomplished, e.g., by comparing RR interval variability (as measure from an ECG signal), or changes in RR interval variability, to a corresponding variability threshold, such that AF is detected when the variability threshold is exceeded. Alternative algorithms for monitoring AF based on RR interval variability are also possible, and within the scope of the present invention. Exemplary techniques for detecting R-waves are discussed above with reference to FIGS. 4A-4E. RR intervals can be determined by determining the duration between consecutive R-wave detections. RR interval variability can be determined by calculating a standard deviation, a pseudo random deviation, root mean-square differences, a range, a interquartile range, a mean difference, a median absolute deviation, an average absolute deviation, etc., of RR intervals measured from an ECG signal. These are just a few examples, which are not meant to be limiting. Other techniques for determining RR interval variability can be used, including but not limited to time domain, frequency domain, and non-linear techniques. RR interval variability is also known as heart rate variability (HRV).

If it is determined at step 506 that it is likely that AF monitoring based on RR interval variability is adversely affected by patient activity, then the process goes to step 510. At step 510, whether and/or how AF monitoring is performed can be modified. In one embodiment, AF monitoring can be inhibited at step 510. In another embodiment, episodes of AF that are detected are ignored at step 510. In still another embodiment, at step 510, information about detected episodes of AF are stored along with an indication that the detected episodes of AF were detected during elevated patient activity. For example, whenever AF is detected, information about the detected AF can be stored in memory (e.g., 294) for later analysis. Such information can include, e.g., data about the time and duration of AF episodes. In accordance with an embodiment, such information can also include an annotation or some other indication that the AF episodes were detected during elevated patient activity, if that is the case. Analysis by a processor and/or a physician can take into account such annotations or indications, e.g., treat such AF detections as having a lower confidence level (e.g., treat such detections as potentially false AF detections).

Figure 6A:
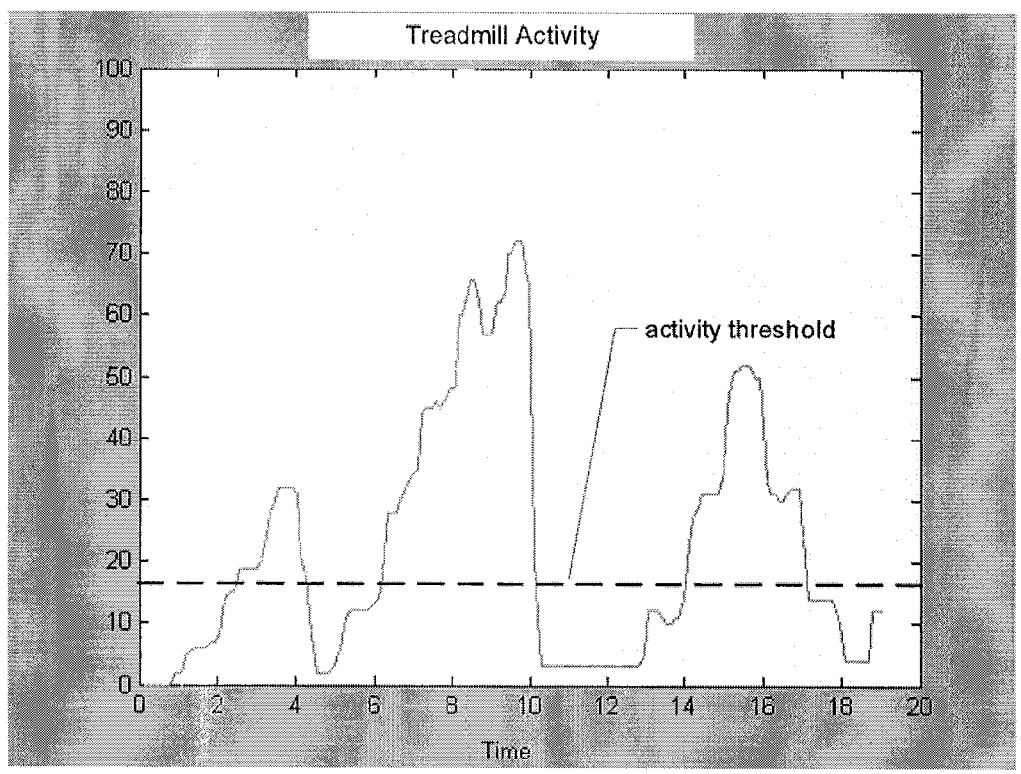
FIGS. 6A and 6B, which are graphs of activity versus time for two different patients performing the same treadmill protocol, illustrate how similar activity may be differently detected depending upon the patient.
Figure 6B:
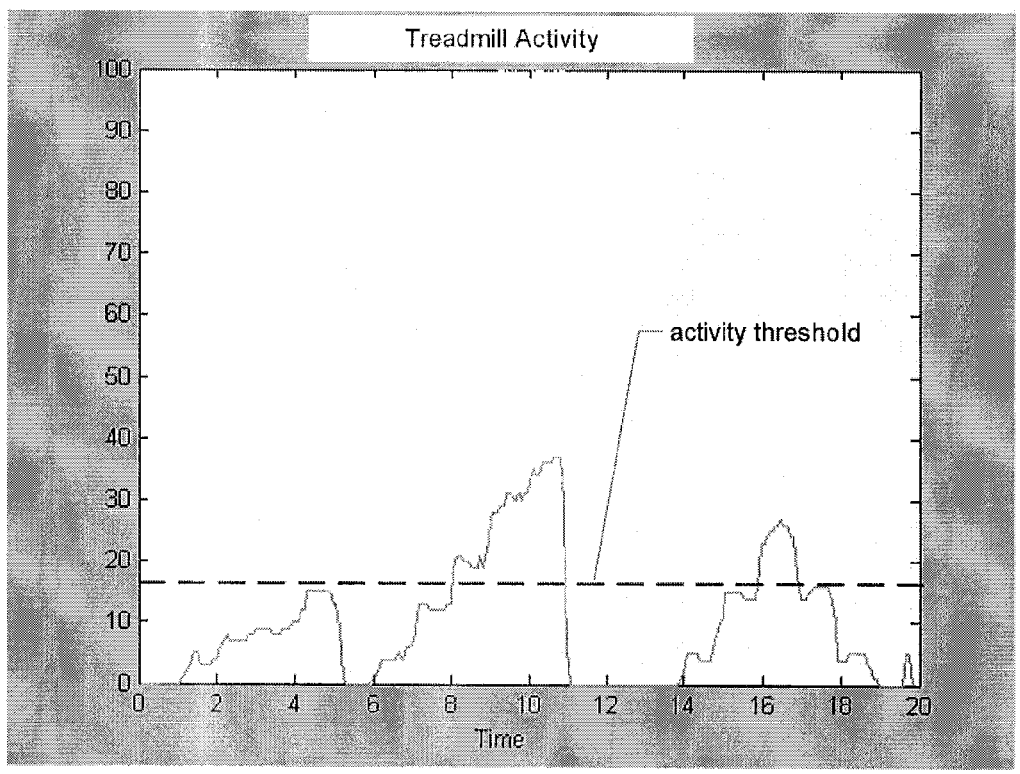

A potential limitation of the embodiment of FIG. 5 will now be described with reference to the graphs of FIGS. 6A and 6B. FIGS. 6A and 6B are graphs of activity level versus time for two different people that performed the same 20 minute treadmill protocol. The exemplary treadmill protocol included having the patient rest for the first minute, walk at a first speed for the second minute, walk at a second speed (faster than the first speed) for the third minute, walk at a third speed (faster than the second speed) for the fourth minute, rest for the fifth minute, walk at further varying speeds during the sixth though tenth minutes, rest for the eleventh through thirteenth minutes, etc.

FIG. 6A shows that when a first patient was asked to perform the 20 minute treadmill protocol, the patient's activity level (as detected using an one dimensional activity sensor) ranged from 0 to 72. In contrast, FIG. 6B shows that when a second patient was asked to perform the same 20 minute treadmill protocol, the second patient's activity level (as detected using the same type of activity sensor) ranged from 0 to 38. FIGS. 6A and 6B also include a dashed horizontal line, illustrative of an exemplary activity threshold.

As can be appreciated from FIGS. 6B and 6A, if a common activity threshold is used for two different patients performing the same activity, whether and how often the activity threshold will be exceeded may significantly vary from patient to patient. Accordingly, the modifying of whether and/or how AF monitoring is performed, at step 508, will vary from patient to patient, even if the patients are performing the same activity. This is not optimal.

Now also assume that for both patients, their activity levels were actual high enough to cause a significant increase in false AF detections during the periods of time between 2 to 4 minutes, 6 to 10 minutes, and 14 to 16 minutes. For the first patient (corresponding to FIG. 6A), the method of FIG. 5 would effectively improve AF monitoring. However, for the second patient (corresponding to FIG. 6B), the method of FIG. 5 would not effectively improved AF monitoring.

Figure 6C:
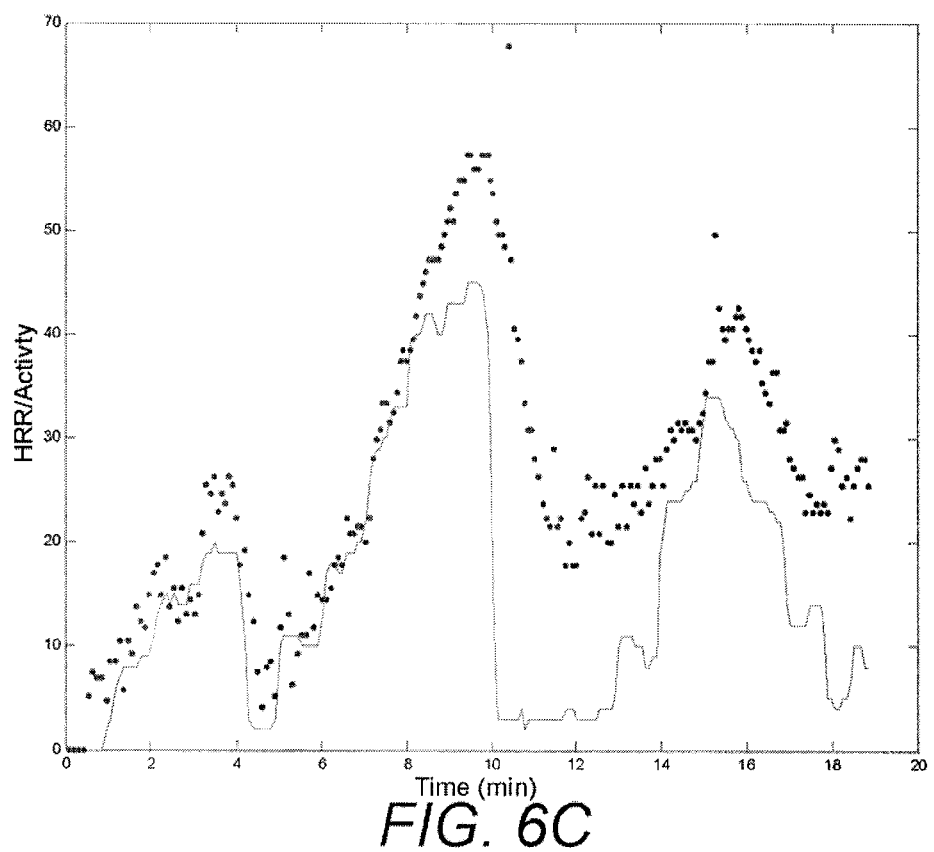
FIG. 6C is a graph that illustrates that heart rate reserve (HRR) and patient activity may be well correlated with one another.
Figure 6D:
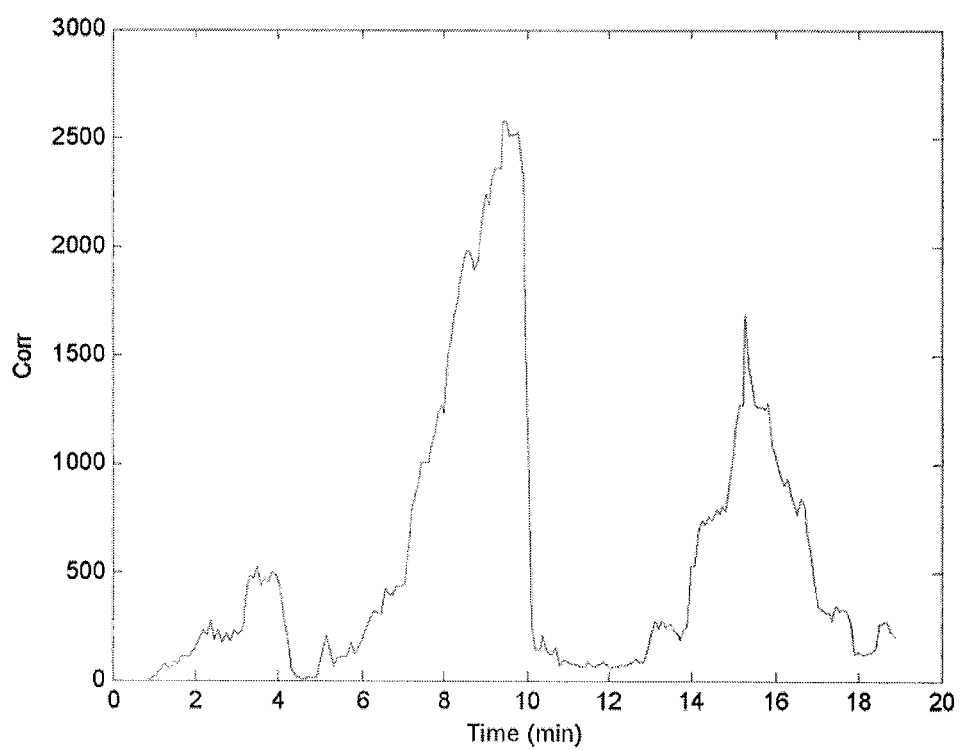
FIG. 6D is a graph of activity correlation values versus time, where the activity correlation values were determined based on the HRR and patient activity levels shown in FIG. 6C.

FIG. 6C is a graph of activity level (the solid line) versus time for a third patient that performed the same 20 minute treadmill protocol discussed above with reference to FIGS. 6A and 6B. FIG. 6C also includes dots that represent values of heart rate reserve (HRR), which is explained in more detail below in the discussion of FIGS. 8-10. Heart rate (HR) varies significantly from patient to patient. HRR is a useful measurement because it provides a normalized heart rate (HR). FIG. 6D is a graph of activity correlation values versus time, where the activity correlation values were determined based on the activity levels and HRR values of FIG. 6C. Exemplary details of how to determine such activity correlation values are described in more detail below with reference to FIGS. 8-10.

FIGS. 6C and 6D illustrates that heart rate reserve (HRR) correlates well with patient activity. The realization that such a correlation exists is advantageously used in certain embodiments of the present invention described below. For example, activity correlation values are used to distinguish between actual patient activity (that will likely adversely affect AF monitoring based on RR interval variability) and background motion, e.g., due to a patient being in a car or train (that would likely not adversely affect AF monitoring based on RR interval variability). Further, because a patient's HRR and activity level would both be high when a patient was actually active, activity correlation values are useful to identify when patient activity would likely adversely affect AF monitoring based on RR interval variability.

Figure 7:
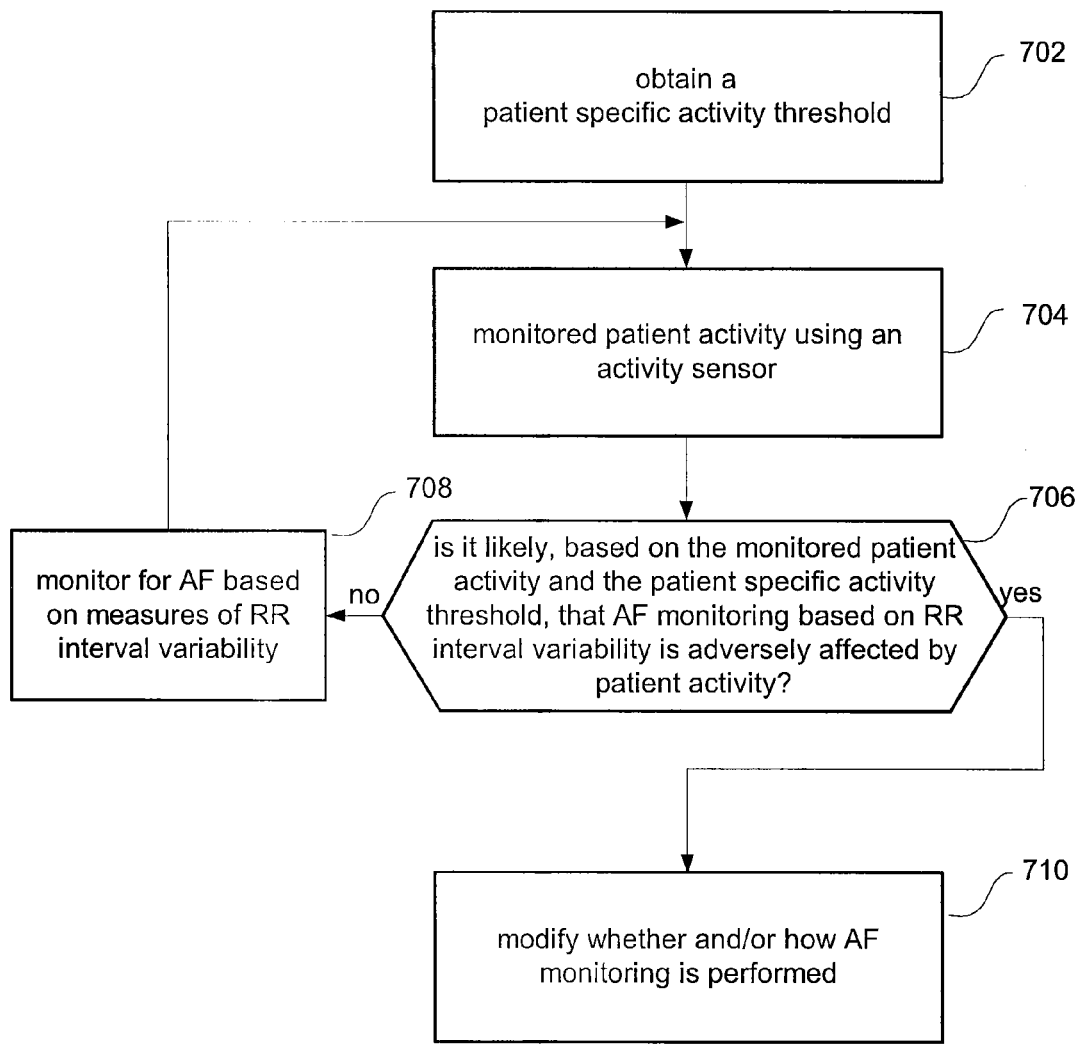
FIG. 7 is a high level flow diagram that describes a method for improved AF monitoring that uses a patient specific activity threshold, in accordance with an embodiment of the present invention.

FIG. 7 will now be used to describe embodiments of the present invention that improve upon the embodiments described above with reference to FIG. 5. More specifically, FIG. 7 is a high level flow diagram used to describe embodiments of the present invention where patient activity, and a patient specific activity threshold, are taken into account when monitoring for AF based on RR interval variability as measured from an electrocardiogram (ECG) signal.

Referring to FIG. 7, at step 702, a patient specific activity threshold is determined, or otherwise obtained. Exemplary details of step 702, according to an embodiment of the present invention, are described below with reference to flow diagram of FIG. 9. At step 704, patient activity is monitored, using an activity sensor (e.g., 118), many examples of which were discussed above. At step 706, there is a determination, based on the monitored patient activity and the patient specific activity threshold, of whether it is likely the AF monitoring based on RR interval variability is adversely affected by patient activity.

In one embodiment, at step 706 the monitored patient activity can be compared to the patient specific activity threshold to determine whether the patient activity exceeds the activity threshold. If the activity threshold is not exceeded, then it can be determined that it is not likely that AF monitoring based on RR interval variability is adversely affected by patient activity, and thus AF monitoring can be performed in that manner at step 708. If the activity threshold is exceeded, then it can be determined that it is likely the AF monitoring based on RR interval variability is adversely affected by patient activity. In a similar manner as was discussed above with reference to step 506, to help distinguish persistent activity from transient activity at step 706, it can be that the patient activity threshold would need to exceed the patient specific activity threshold for at least an entry duration for there to be a determination that AF monitoring based on RR interval variability is adversely affected by patient activity. Further, after it has been determined that it is likely that AF monitoring based on RR interval variability is adversely affected, it can thereafter be determined that it is no longer likely that AF monitoring based on RR interval variability is adversely affected, when the monitored patient activity does not exceed the patient specific activity threshold for at least an exit duration. Preferably the exit duration is longer than the entry duration. For example, the entry duration can be 20 seconds, and the exit duration can be 60 seconds. Such durations can be programmed into the device. The exemplary duration values are not meant to be limiting.

Figure 8:
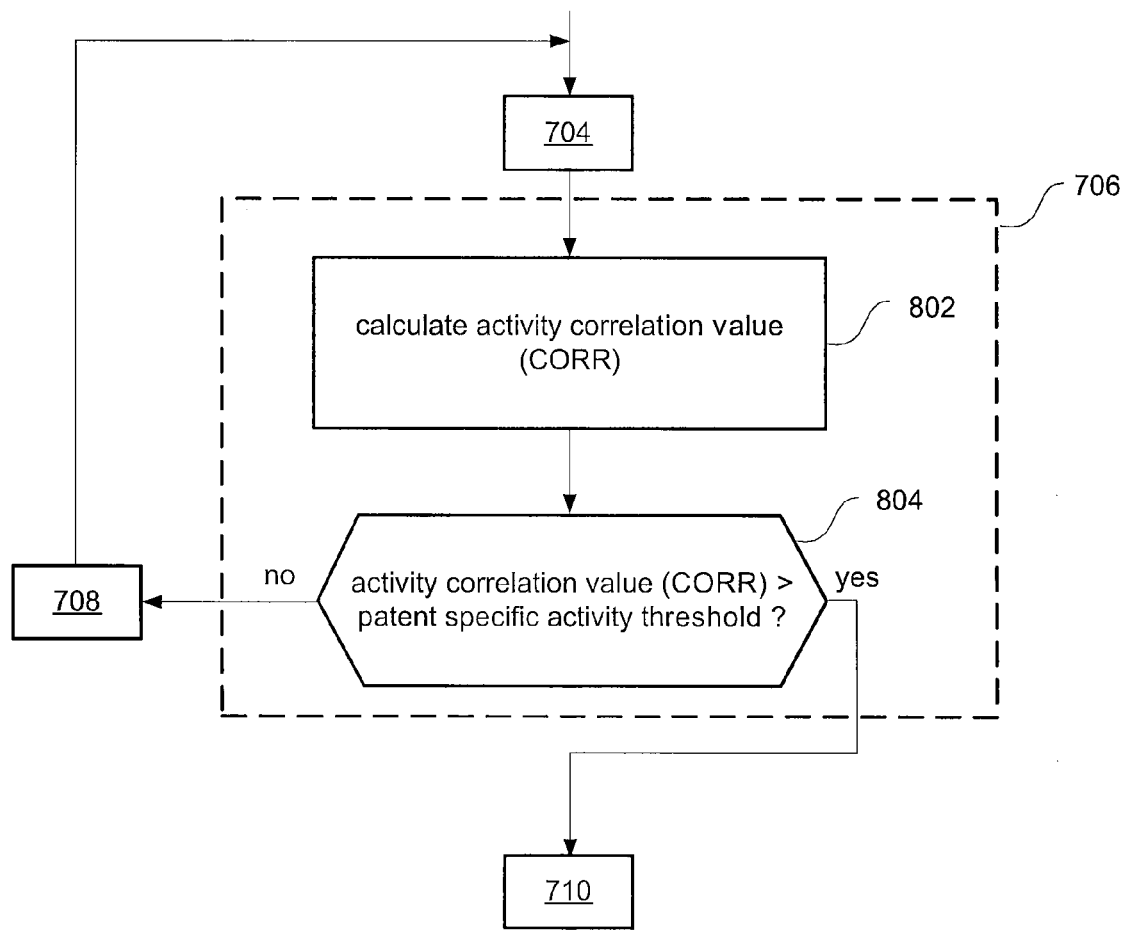
FIG. 8 is a high level flow diagram that describes a method for determining whether a patient's current activity level exceeds a patient specific activity threshold, which is one of the steps in FIG. 7.

Exemplary details of step 706, according to an alternative embodiment of the present invention, are described below with reference to the flow diagram of FIG. 8. Briefly, in the embodiment described with reference to FIG. 8, activity correlation values are determine based on the monitored patient activity and corresponding heart rate data. The activity correlation values are compared to the patient specific activity threshold. When the activity correlation values exceed the patient specific activity threshold, it is determined that it is likely that AF monitoring based on RR interval variability is adversely affected by patient activity. Otherwise, it is determined that it is not likely AF monitoring based on RR interval variability is adversely affected by patient activity. Alternative algorithms are also possible, and within the scope of the present invention.

If it is determined that it is not likely AF monitoring based on RR interval variability is adversely affected by patient activity, then, at step 708 monitoring for AF based on RR interval variability is performed. For example, at step 708 monitoring for AF can be accomplished by comparing RR interval variability (determined based on the ECG signal), or changes in RR interval variability, to a corresponding variability threshold, such that AF is detected when the variability threshold is exceeded. Alternative algorithms are also possible, and within the scope of the present invention.

If it is determined at step 706 that it is likely that AF monitoring based on RR interval variability is adversely affected by patient activity, then the process goes to step 710. At step 710, whether and/or how AF monitoring is performed can be modified, in a similar manner as was discussed above with reference to step 510. In one embodiment, AF monitoring can be inhibited at step 710. In another embodiment, episodes of AF that are detected are ignored at step 710. In still another embodiment, at step 710, information about detected episodes of AF are stored along with an indication that the detected episodes of AF were detected during elevated patient activity. For example, whenever AF is detected, information about the detected AF can be stored in memory, e.g., for later analysis. Such information can include, e.g., data about the time and duration of AF episodes. In accordance with an embodiment, such information can also include an annotation or some other indication that the AF episode was detected during elevated patient activity, if that is the case. Analysis by a processor and/or a physician can take into account such annotations or indications, e.g., treat such AF detections as having a lower confidence level (e.g., treat such detections as potentially false AF detections).

As mentioned above, exemplary details of step 706 are described with reference to FIG. 8, which will now be discussed. Referring to FIG. 8, at step 802, current patient heart-rate and current patient activity level measurements are used to calculate a current activity correlation value ($CORR_{current}$) using the following equation:

$$CORR_{current} = HRR \times (ACT_{current} - ACT_{offset}),$$

where HRR (heart rate reserve) can be obtained as described below with reference to step 908 of FIG. 9; $ACT_{current}$ is the activity measurement output by an activity sensor; and $ACT_{offset}$ can be obtained as described below with reference to step 1008 of FIG. 10.

In a specific embodiment, the heart rate and activity level measurements are taken periodically, for example, every "x" seconds or "n" heart beats where "x" and "n" are programmed and may be small quantities, such as 5 seconds and 3 heart beats, where resolution increases accuracy of detection. Periodic sampling is preferred over continuous measurements in order to conserve memory. In step 804, the current activity correlation value ($CORR_{current}$) is compared to the patient specific activity threshold (ACT THR). If the current correlation value does not exceed the patient specific activity threshold, the process returns to the step 704, and another current activity correlation value is calculated at step 802 using the next periodic current heart-rate and activity level measurements, and the comparison process repeats. When the current activity correlation value exceeds the patient specific activity threshold, then it is determined that the patient activity exceeds the patient activity threshold, and step 710 occurs, which was explained in detail above. It can also be that the current activity correlation value would need to exceed the patient specific activity threshold for at least an entry duration for it to be determined that AF monitoring based on RR interval variability is adversely affected by patient activity. Further, after it has been determined that it is likely that AF monitoring based on RR interval variability is adversely affected, it can thereafter be determined that it is no longer likely that AF monitoring based on RR interval variability is adversely affected, when the current activity correlation value does not exceed the patient specific activity threshold for at least an exit duration. Some additional details of entry and exit durations are provided above in the discussions of steps 506 and 706 with reference to FIGS. 5 and 7.

In accordance with an embodiment of the present invention, the patient specific activity threshold can be obtained at step 702 using the method described below with reference to the high level flow diagram of FIG. 9. More specifically, FIG. 9 is a high level flow diagram that is used to describe a method for determining a patient specific activity threshold. The patient specific activity threshold (ACT THR) can be determined, e.g., upon implant of a device, and may be periodically updated to account for changes in the patient's condition and sensitivity of the device sensors. The method involves the collection and analysis of patient data over a period of time, referred to as the "activity threshold time period."

Referring to FIG. 9, at step 902, the activity threshold time period is determined. This time period may be programmed into the device by the physician and is long enough to allow for the collection and analysis of a quantity of patient data sufficient to avoid the potential for inaccurate activity threshold calculations due to possible noise and atypical patient activity. In one configuration, the activity threshold time period is 7 days. At step 904 the activity threshold time period is partitioned into first sub-time periods, for example 1 day time periods, in the case of a 7 day activity threshold time period. At step 906 the first sub-time periods are partitioned into second sub-time periods, for example, 1 hour time periods in the case of 1 day first sub-time periods. As described above with reference to the determination of patient-specific offset parameters, the use of sub-time periods is not necessary, but is preferred in order to conserve memory space.

At step 908, for each second sub-time time period, heart rate and activity level are periodically measured, for example every 10 seconds. The heart rate measurements are used, in turn, to calculate a plurality of heart-rate reserve values using the following equation:

$$HRR = \frac{HR - HR_{baseline}}{\text{Age Compensated Maximum } HR - HR_{baseline}} \times 100$$

Heart-rate reserve (HRR) is preferably used in the method instead of heart rate in order to utilize a heart rate measurement that is normalized across the patient population. Such normalization accounts for the fact that the same heart rate may correspond to different activity states for different people. For example, a heart rate of 90 beats per minute may correspond to sitting for one person and walking for another person. In the equation indicated above, HR (heart rate) and HRbaseline may be obtained by any suitable method. For example, HR can be obtained based on an average of a plurality of RR intervals. An exemplary technique for determining $HR_{baseline}$ is described with reference to FIG. 10. The age compensated maximum heart rate can be calculated by the formula: (220−age).

While the above HRR equation is expressed in terms of HR parameters, actual implementation of the above HRR equation may involve the use of heart rate interval (HRI) calculations. In terms of HRI, the equation for HRR becomes:

$$HRR = \frac{\frac{HRI_{min}}{HRI} \times (HRI_{baseline} - HRI)}{HRI_{baseline} - HRI_{min}} \times 100$$

In the equation indicated above, HRI (heart rate interval) may be obtained by any suitable method; $HRI_{min}$ may be obtained using the equation: 60,000/(220−age) and $HRI_{baseline}$ may be obtained by converting the $HR_{baseline}$ measurement described with reference to FIG. 10 into a heart rate interval measurement.

In order to reduce rounding errors when processing the above equation, it is desirable to perform all multiplication functions first in order to make the numerator larger than the denominator. Considering the range of HRI in milliseconds, a 2 byte by 2 byte multiplier may be used to perform the multiplication operations. In addition, there are several multiplication and division operations in the HRR equation, which may impact processor duty cycle.

In an alternate embodiment, processing efficiency may be enhanced by obtaining an approximated heart-rate reserve using the following equation:

$$HRR_{approx} = HR - HR_{baseline}$$

which in terms of HRI translates to:

$$HRR_{approx} = (60,000/HRI) - (60,000/HRI_{baseline})$$

This calculation reduces the number of arithmetic operations and may be completed using a 1 byte by 1 byte multiplier, thereby reducing the processor duty cycle.

Continuing with step 908, the activity level measurements can be used to calculate a plurality of activity correlation values using the following equation:

$$CORR_{sub\text{-}time} = HRR \times (ACT_{sub\text{-}time} - ACT_{offset})$$

where $ACT_{sub\text{-}time}$ is the activity measurement provided by the activity sensor during the sub-time period; and $ACT_{offset}$ is obtained as described below with reference to step 1008 of FIG. 10. Note that $HRR_{approx}$ may be used in place of HRR in the $CORR_{sub\text{-}time}$ calculation.

The sub-time correlation values can be analyzed using, for example, a histogram analysis similar to that described below with respect to FIG. 10, step 1006, to identify the sub-time correlation value appearing most frequent within the second sub-time period. A second sub-time activity threshold can be set at X % above the most frequent correlation value, where X is programmable and may be for example, 70, 80 or 90. Setting the second sub-time activity threshold as a percentage above the most frequent correlation value provides for the filtering of noise and allows for a deterministic approach towards a threshold that encompasses a level of activity. An example of a 1 hour histogram is shown in FIG. 11.

Continuing with FIG. 9, at step 910 after identifying the plurality of second sub-time period activity thresholds, e.g., twenty-four, 1 hour thresholds in the case of a 1 day first sub-time period, the median of the plurality of second sub-time period activity thresholds is identified as the activity threshold for that first sub-time period. While other statistical measurements may be used, the median value can be chosen for robustness of the threshold, which will not be changed by several hours of atypical activities. The process is repeated for each first sub-time period to identify a plurality of first sub-time period activity thresholds. Thus in the case of a 7 day activity threshold time period, seven, 1 day activity thresholds would be determined. In step 912, at the end of the total activity threshold time period, e.g., 7 days, the patient specific activity threshold (ACT THR) is set equal to the average of the plurality of first sub-time period, e.g., 1 day, activity thresholds. While other statistical measures may be used, an average can be chosen to account for weekday and weekend difference of activity patterns.

Figure 10:
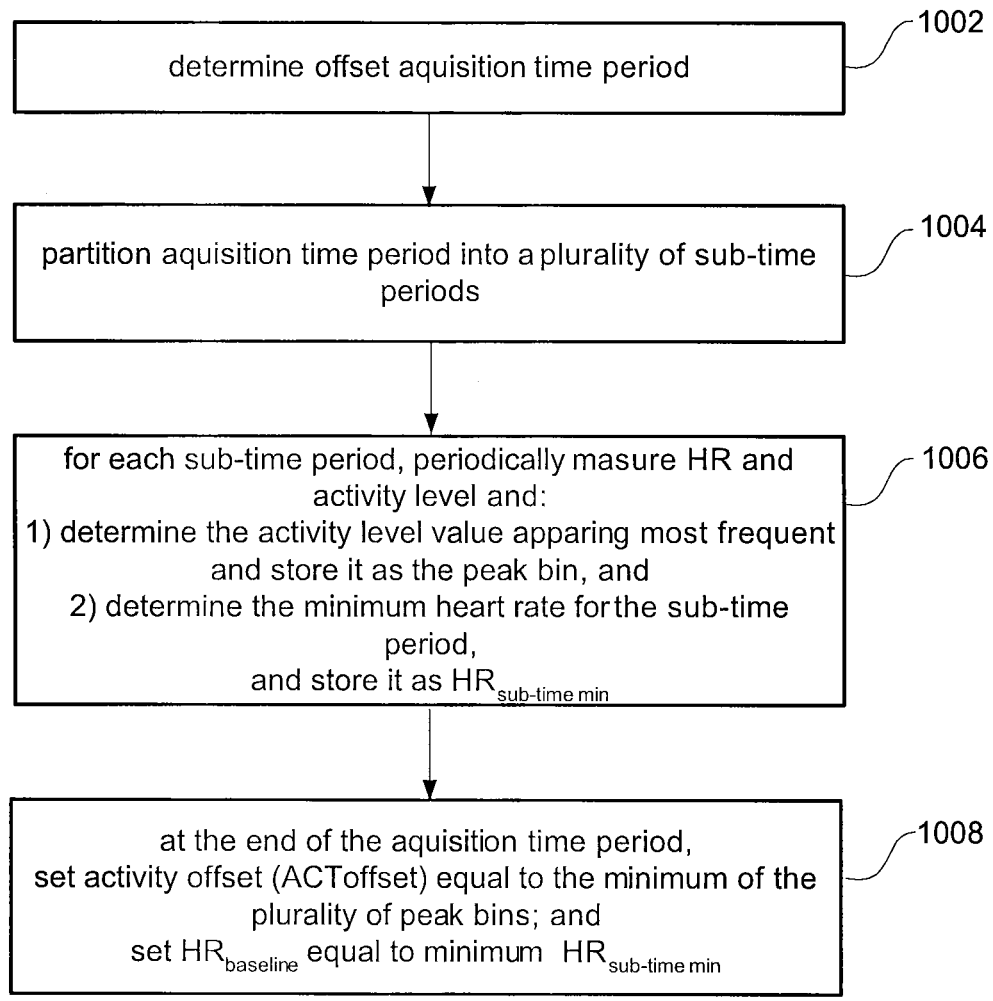
FIG. 10 is a high level flow diagram that describes a method for detecting activity offset and heart rate baseline values, which can be used to determine a patient specific activity threshold.
Figure 11:
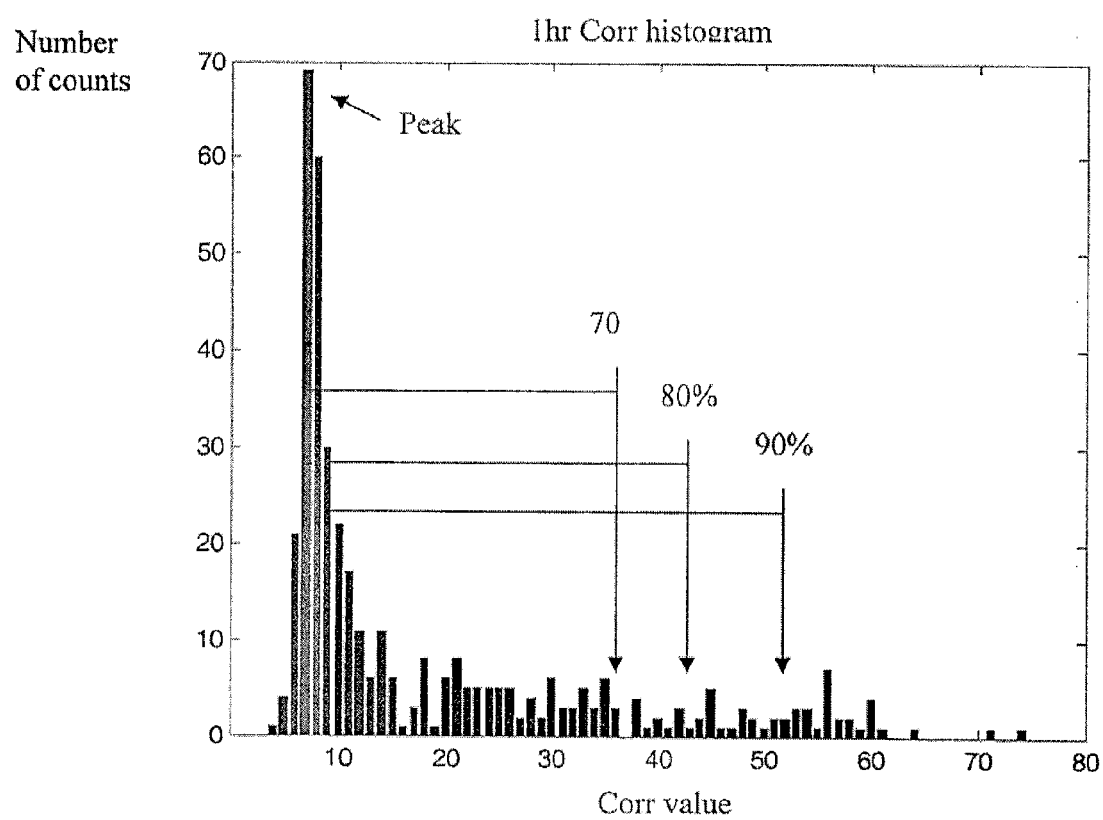
FIG. 11 is an exemplary histogram of activity correlation values that can be used to determine a patient specific activity threshold.

The high level flow diagram of FIG. 10 will now be used to describe an embodiment for determining patient specific offset parameters ($ACT_{offset}$ and $HR_{baseline}$). The data collection of offset parameters can be initiated, e.g., upon implant of the device, and may be periodically updated to account for changes in the patient's condition and sensitivity of the device sensors. The method involves the collection and analysis of patient data over a period of time, referred to as the "offset-acquisition time period."

Referring to FIG. 10, at step 1002, an offset acquisition time period is determined. This time period may be programmed into the device by the physician and is long enough to allow for the collection and analysis of a quantity of patient data sufficient to avoid the potential for inaccurate parameter offset calculations due to possible noise and atypical patient activity. In one configuration, the offset acquisition time period is 24 hours. At step 1004 the offset acquisition time period is partitioned into sub-time periods, for example, 1 hour time periods in the case of a 24 hour offset acquisition time period. Though the use of sub-time periods is not necessary, as will be apparent from the following explanation, sub-time periods conserve memory space.

At step 1006, for each sub-time period, heart rate and activity level are periodically measured, for example every 10 seconds. The patient's heart rate may be determined by any suitable method. Many variations on how to determine heart rate are known to those of ordinary skill in the art, and any of these of reasonable accuracy may be used. For example, heart rate can be determined by measurement of an R-R interval cycle length, which is the inverse of heart rate. As used herein, the heart rate (in beats per minute) can be seen as the inverse to cycle length, determined by 60,000 divided by the cycle length (in milliseconds). This is just an example, which is not meant to be limiting.

The activity level of the patient may also be determined by any suitable method. For example, the activity level may be determined by an accelerometer, piezoelectric crystal, minute ventilation, or a derivative thereof, such as the sensor indicated rate. In one embodiment, activity level is determined using the activity sensor 118.

Continuing with FIG. 10, at step 1006, for each sub-time period, in an exemplary type of activity data analysis, a histogram of activity level data over the sub-time period is created. At the end of the sub-time period, the activity level value appearing most frequent within the 1 hour histogram is saved as the "peak bin." In addition, at the end of each sub-time period, in an exemplary type of heart-rate data analysis, a minimum heart rate measured in the sub-time period is stored as $HR_{sub\text{-}time\ min}$. The $HR_{sub\text{-}time\ min}$ is not necessarily the lowest heart rate measured but instead may be a heart rate that is close to the lowest measured rate in order to account for possible noise.

At step 1008, at the end of the time period, the activity offset parameter ($ACT_{offset}$) can be determined to be the minimum of the plurality of activity-level "peak bins." The heart rate offset ($HR_{baseline}$) can be determined to be the minimum of the $HR_{sub\text{-}time\ min}$'s measured during the period of time.

It can be appreciated from the above equations that activity correlation (CORR) values will be relatively high when HR and ACT are both relatively high, and will be relatively low when at least one of HR and ACT are relatively low. Thus, if HR and ACT are both relatively high, the CORR values should exceed the patient specific activity threshold, and it should be determined that it is likely that AF monitoring based on RR interval variability is adversely affected by patient activity. In contrast, if at least one of HR and ACT are relatively low, the CORR values should not exceed the patient specific activity threshold. A relatively low HR, as the term is being used, is a HR value at or closed to a patient's $HR_{baseline}$. A relatively low ACT, as the term is being used, is an ACT value at or close to the $ACT_{offset}$.

Figure 12:
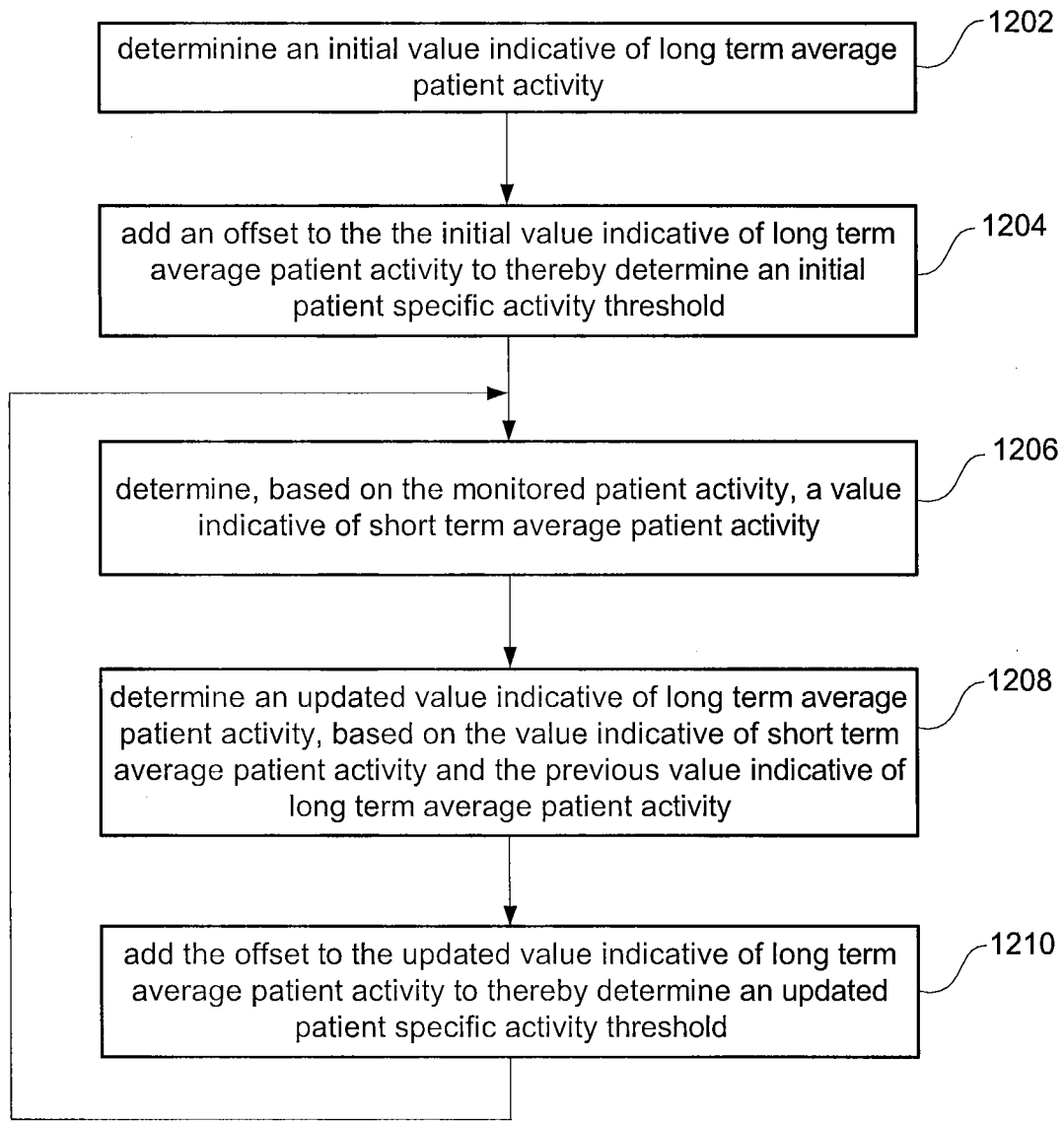
FIG. 12 is a high level flow diagram that describes another method for determining a patient specific activity threshold that can be used in the method of FIG. 7.

FIG. 12 is a high level flow diagram that describes another method for determining a patient specific activity threshold that can be used in the method described with reference to FIG. 7. Referring to FIG. 12, at step 1202 an initial value indicative of long term average patient activity is determined. This might take place when a device is first powered up or reset, and thus has not yet had a chance to determine true long term average patient activity. For example, initialization can take n cardiac cycles (e.g., n=30). Where n=1: an activity sensor short term average (n) can equal the maximum sensor reading during the $1^{st}$ cardiac cycle; and an activity sensor long term average (n) can similarly equal the maximum sensor reading during the $1^{st}$ cardiac cycle. When n=2 to 30: the activity sensor short term average (n) can equal $\frac{1}{16}$*(the maximum sensor reading during the $n^{th}$ cardiac cycle)+$\frac{15}{16}$*(activity sensor short term average for the n−$1^{th}$ cardiac cycle); and the activity sensor long term average (n) can equal $\frac{1}{2}$*((activity sensor long term average (n−1))+(activity sensor short term average (n)). This is just an example of how to determine an initial value indicative of long term average patient activity, which is not meant to be limiting. Additionally, sensor trim and/or gain values can be used to normalize or otherwise adjust the above discussed sensor readings as desired.

Referring to FIG. 12, at step 1204, an initial patient specific activity threshold can be determined by adding an offset to the initial value indicative of long term average patient activity. Such an offset is used to control the sensitivity of the algorithm, so that relatively minor patient activity does not cause the device to prematurely determine that AF monitoring based on RR interval variability is adversely affected by patient activity (e.g., at step 706). The offset, which can be programmable, can be chosen for a patient population based on empirical data, or the offset can be defined for a specific patient. The offset can also be adjusted as desired, by reprogramming the offset.

Following initialization, the patient specific activity threshold is updated from time to time, e.g., once every cardiac cycle (or once every m cardiac cycles), at steps 1206-1210. At step 1206, a value indicative of short term patient activity is determined. For example, an activity sensor short term average (n) can equal ($1/16$)*(the maximum sensor reading during the $n^{th}$ cardiac cycle)+($15/16$)*(the activity sensor short term average (n-1)). At step 1208, an updated value indicative of long term patient activity is determined based on the previous value indicative of long term patient activity and the value indicative of short term patient activity, which was determined at step 1206. For example, an activity sensor long term average (n) can equal ($65535/65536$)*(activity sensor long term average (n-1))+($1/65536$)*(activity sensor short term average (n)). More generally, a running weighted average of long term and short term average patient activity, where the long term average is weighted more heavily, can be used to repeatedly update the value indicative of long term average patient activity. As mentioned above, sensor trim and/or gain values can be used to normalize or otherwise adjust the above discussed sensor readings.

At step 1210, the offset is added to the updated value indicative of long term average patient activity (determined at step 1208) to determine an updated patient specific activity threshold. As mentioned above, the offset is used to control the sensitivity of the algorithm. In accordance with an embodiment, the offset is at least twice is large as the value indicative of long term average patient activity, and may be significantly larger (e.g., more than 5 times larger).

Where episodes of AF are detected, information about the episodes can be stored for later analysis. This can include, for example, storing information about the RR interval variability, information about the times and durations of the AF episodes, etc. If a device is appropriately equipped, a therapeutic response can be triggered to attempt to convert the AF to normal sinus rhythm. For example, atrial anti-tachycardia pacing (AATP) can be delivered. For another example, if the implantable device included a drug pump, appropriate medication can be dispensed. Additionally, or alternatively, the stored information about AF episodes can be analyzed to adjust a drug therapy and/or to determine whether ablation treatment should be performed.

As mentioned above, in certain embodiments information about detected episodes of AF can be stored along with an indication that the detected episodes of AF were detected during elevated patient activity (i.e., when the activity threshold, which is preferably patient specific, is exceeded). The stored information about episodes of AF that were detected during elevated patient activity can then be analyzed, in order to determine which detected episodes where actually AF episodes and which detected episodes were detected due to patient activity. Thereafter, the variability threshold, used to detected episodes of AF, can be adjusted based on results of the analyzing. For example, it may be determined that if the variability threshold were increased by a certain amount, AF can be detected based on RR interval variability with increased accuracy. Additionally, or alternatively, the activity threshold can be adjusted based on the stored information.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for use with a system that monitors for atrial fibrillation (AF) based on RR interval variability as measured from an electrocardiogram (ECG) signal, the method comprising:
   (a) obtaining a patient specific activity threshold;
   (b1) monitoring patient activity with an activity sensor not based on a cardiac electrical signal;
   (b2) monitoring for AF based on RR interval variability in said ECG signal;
   (c) determining, based on the monitored patient activity and the patient specific activity threshold, when it is likely that AF monitoring based on RR interval variability is adversely affected by patient activity, wherein step (c) includes:
      (c.1) determining activity correlation values based on both the monitored patient activity and heart rate reserve values corresponding to the monitored patient activity; and
      (c.2) determining that it is likely that AF monitoring based on RR interval variability is adversely affected, when the activity correlation values exceed the patient specific activity threshold; and
   (d) modifying whether and/or how AF monitoring is performed, when it has been determined that it is likely that AF monitoring based on RR interval variability is adversely affected by patient activity.

2. The method of claim 1, wherein when it has been determined at step (c) that it is likely that AF monitoring based on RR interval variability is adversely affected, step (d) comprises one of the following:
   (d.1) inhibiting AF monitoring;
   (d.2) ignoring detected episodes of AF; and
   (d.3) storing information about detected episodes of AF along with an indication that the detected episodes of AF were detected during elevated patient activity.

3. The method of claim 1, wherein when it has been determined at step (c) that it is likely that AF monitoring based on RR interval variability is adversely affected, step (d) comprises:
storing information about detected episodes of AF along with an indication that the detected episodes of AF were detected during elevated patient activity;
analyzing the stored information about episodes of AF that were detected during elevated patient activity, in order to determine which detected episodes were actually AF episodes and which detected episodes were detected due to patient activity; and
adjusting a variability threshold, used to detected episodes of AF, based on results of the analyzing.

4. The method of claim 1, wherein step (c) further includes, after it has been determined at (c.2) that it is likely that AF monitoring based on RR interval variability is adversely affected:
determining that it is no longer likely that AF monitoring based on RR interval variability is adversely affected, when the activity correlation values do not exceed the activity threshold for at least a specified duration.

5. The method of claim 1, wherein step (a) includes:
(a.1) determining, based on the monitored patient activity, a value indicative of long term average patient activity; and
(a.2) determining the patient specific activity threshold by adding an offset to the value indicative of long term average patient activity.

6. The method of claim 5, wherein step (a.1) includes:
(i.) determining, based on the monitored patient activity, a value indicative of short term average patient activity; and
(ii.) determining, based on the value indicative of short term average patient activity and a previous value indicative of long term average patient activity, the value indicative of long term average patient activity.

7. The method of claim 5, wherein the offset is at least twice the value indicative of long term average patient activity.

8. The method of claim 1, wherein step (a) includes determining the patient specific activity threshold based on historical patient heart-rate data and historical patient activity data.

9. The method of claim 8, wherein step (a) includes:
calculating a plurality of time-period activity thresholds over a period of time; and
calculating the patient specific activity threshold value based on the plurality of time-period activity thresholds;
wherein the patient specific activity threshold is based on the average of the plurality of time-period activity thresholds.

10. The method of claim 9, wherein the calculating a plurality of time-period activity thresholds over a period of time comprises:
calculating a plurality of correlation values derived from patient heart-rate, patient activity, a heart-rate offset parameter and an activity offset parameter over a plurality of portions of the period of time;
identifying a peak correlation value for each of the plurality of portions; and
for each of the plurality of portions, obtaining a time-period activity threshold as a function of the peak correlation value corresponding to the portion.

11. The method of claim 10, wherein the heart-rate offset parameter is one of:
a minimum heart rate measured over an offset acquisition period of time; and
a minimum activity value of a plurality of maximum activity values measured over an offset acquisition period of time.

12. The method of claim 1, wherein when it has not been determined that it is likely that AF monitoring based on RR interval variability is adversely affected, then monitoring for AF comprises:
measuring RR intervals from an ECG signal;
determining RR interval variability based on the measured RR intervals;
comparing the RR interval variability to a variability threshold; and
detecting AF when the RR interval variability exceeds the variability threshold.

13. The method of claim 1, wherein when it has not been determined that it is likely that AF monitoring based on RR interval variability is adversely affected, then monitoring for AF comprises:
obtaining a baseline RR interval variability;
measuring RR intervals from an ECG signal;
determining RR interval variability based on the measured RR intervals;
determining an increase in RR interval variability by determining a difference between the determined RR interval variability and the baseline RR interval variability;
comparing the increase in RR interval variability to a variability threshold; and
detecting AF when the increase in RR interval variability exceeds the variability threshold.

14. A system, comprising:
an atrial fibrillation (AF) monitor configured to monitor for AF based on RR interval variability as measured from an ECG signal;
memory to store information about detected episodes of AF;
at least one activity sensor configured to monitor patient activity without using a cardiac electrical signal;
at least one processor configured to determine:
activity correlation values based on both the monitored patient activity and heart rate reserve values corresponding to the monitored patient activity; and
that it is likely that AF monitoring based on RR interval variability is adversely affected, when the activity correlation values exceed the patient specific activity threshold; and
wherein whether to or how to monitor for AF is modified, when the at least one processor determines that it is likely that AF monitoring based on RR interval variability is adversely affected by patient activity.

15. The system of claim 14, wherein the AF monitor is implemented by the at least one processor.

16. The system of claim 14, wherein the system is an implantable system configured to obtain the ECG signal using implantable extracardiac sensing electrodes.

17. The system of claim 14, wherein the system is a non-implantable system configured to obtain the ECG signal using surface electrodes.

18. The system of claim 14, wherein when it has been determined that it is likely that AF monitoring based on RR interval variability is adversely affected, at least one of following occurs:
the AF monitor is inhibited;
episodes of AF detected by the AF monitor are ignored; and
information about episodes of AF detected by the AF monitor are stored in the memory along with an indication that the detected episodes of AF were detected during elevated patient activity.

19. A method for use with a system that monitors for atrial fibrillation (AF) based on RR interval variability as measured from an electrocardiogram (ECG) signal, the method comprising:
  (a) obtaining a patient specific activity threshold;
  (b1) monitoring patient activity with an activity sensor not based on a cardiac electrical signal;
  (b2) monitoring for AF based on RR interval variability in said ECG signal;
  (c) determining, based on both the monitored patient activity and the patient specific activity threshold, when it is likely that AF monitoring based on RR interval variability is adversely affected by patient activity, wherein step (c) includes:
    (c.1) determining activity correlation values based on both the monitored patient activity and corresponding heart rate data; and
    (c.2) determining that it is likely that AF monitoring based on RR interval variability is adversely affected, when the activity correlation values exceed the patient specific activity threshold;
  (d) modifying whether and/or how AF monitoring is performed, when it has been determined that it is likely that AF monitoring based on RR interval variability is adversely affected by patient activity, wherein step (d) comprises:
    storing information about detected episodes of AF along with an indication that the detected episodes of AF were detected during elevated patient activity;
    analyzing the stored information about episodes of AF that were detected during elevated patient activity, in order to determine which detected episodes were actually AF episodes and which detected episodes were detected due to patient activity; and
    adjusting a variability threshold, used to detected episodes of AF, based on results of the analyzing.

20. The method of claim 19, wherein step (c.2) includes determining that it is likely that AF monitoring based on RR interval variability is adversely affected, when the activity correlation values exceed the patient specific activity threshold for at least a specified first duration.

21. The method of claim 19, wherein step (c) further includes, after it has been determined at (c.2) that it is likely that AF monitoring based on RR interval variability is adversely affected:
  determining that it is no longer likely that AF monitoring based on RR interval variability is adversely affected, when the activity correlation values do not exceed the patient specific activity threshold for at least a specified second duration,
  wherein the specified second duration is longer than the specified first duration.

* * * * *